United States Patent
Ullrich, Jr. et al.

(10) Patent No.: US 11,096,796 B2
(45) Date of Patent: Aug. 24, 2021

(54) INTERBODY SPINAL IMPLANT HAVING A ROUGHENED SURFACE TOPOGRAPHY ON ONE OR MORE INTERNAL SURFACES

(71) Applicant: Titan Spine, Inc., Warsaw, IN (US)

(72) Inventors: Peter F. Ullrich, Jr., Neenah, WI (US); Kevin W. Gemas, Thiensville, WI (US); Chad J. Patterson, Port Washington, WI (US); Jennifer M. Schneider, Germantown, WI (US)

(73) Assignee: TITAN SPINE, LLC, Mequon, WI (US)

( * ) Notice: Subject to any disclaimer, the term of this patent is extended or adjusted under 35 U.S.C. 154(b) by 1021 days.

(21) Appl. No.: 13/784,144

(22) Filed: Mar. 4, 2013

(65) Prior Publication Data

US 2013/0282122 A1 Oct. 24, 2013

Related U.S. Application Data

(63) Continuation-in-part of application No. 13/572,077, filed on Aug. 10, 2012, now Pat. No. 8,496,710,
(Continued)

(51) Int. Cl.
*A61F 2/44* (2006.01)
*A61F 2/30* (2006.01)
(Continued)

(52) U.S. Cl.
CPC ........ *A61F 2/4465* (2013.01); *A61F 2/30965* (2013.01); *A61F 2002/2817* (2013.01);
(Continued)

(58) Field of Classification Search
CPC .......... A61F 2/44; A61F 2/4455; A61F 2/446; A61F 2/4465; A61F 2/447;
(Continued)

(56) References Cited

U.S. PATENT DOCUMENTS

| | | |
|---|---|---|
| 4,314,876 A | 2/1982 | Kremer et al. |
| 4,834,757 A | 5/1989 | Brantigan |

(Continued)

FOREIGN PATENT DOCUMENTS

| | | |
|---|---|---|
| EP | 0599419 | 6/1994 |
| EP | 0916323 A1 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.
(Continued)

*Primary Examiner* — Amy R Sipp
(74) *Attorney, Agent, or Firm* — Womble Bond Dickinson (US) LLP

(57) ABSTRACT

Interbody spinal implants comprise internal sidewalls having a roughened surface topography. The internal sidewalls may be those that surround a substantially hollow implant center, including the sidewalls of a vertical aperture and sidewalls of a transverse aperture. The roughened surface topography comprises macro, micro, and nano features that comprise an amplitude, a peak to valley height, and spacing.

20 Claims, 37 Drawing Sheets

Related U.S. Application Data which is a continuation of application No. 12/151,198, filed on May 5, 2008, now Pat. No. 8,262,737, which is a continuation-in-part of application No. 11/123,359, filed on May 6, 2005, now Pat. No. 7,662,186, application No. 13/784,144, which is a continuation-in-part of application No. 13/107,886, filed on May 14, 2011, now abandoned.

(60) Provisional application No. 61/334,853, filed on May 14, 2010.

(51) Int. Cl.
  *A61F 2/28* (2006.01)
  *A61F 2/46* (2006.01)

(52) U.S. Cl.
  CPC ............... *A61F 2002/2835* (2013.01); *A61F 2002/30014* (2013.01); *A61F 2002/3084* (2013.01); *A61F 2002/30133* (2013.01); *A61F 2002/30405* (2013.01); *A61F 2002/30593* (2013.01); *A61F 2002/30604* (2013.01); *A61F 2002/30772* (2013.01); *A61F 2002/30785* (2013.01); *A61F 2002/30836* (2013.01); *A61F 2002/30838* (2013.01); *A61F 2002/30892* (2013.01); *A61F 2002/30906* (2013.01); *A61F 2002/30925* (2013.01); *A61F 2002/448* (2013.01); *A61F 2002/4629* (2013.01); *A61F 2220/0025* (2013.01); *A61F 2230/0015* (2013.01); *A61F 2250/0018* (2013.01); *A61F 2310/00017* (2013.01); *A61F 2310/00023* (2013.01)

(58) Field of Classification Search
  CPC .......... A61F 2/30767; A61F 2002/4475; A61F 2002/30321; A61F 2002/30324; A61F 2002/30322; A61F 2002/30028; A61F 2002/30029; A61F 2002/3093; A61F 2002/30838; A61F 2002/3084
  See application file for complete search history.

(56) References Cited

U.S. PATENT DOCUMENTS

| | | |
|---|---|---|
| 4,904,261 A | 2/1990 | Dove et al. |
| 5,015,247 A | 5/1991 | Michelson |
| 5,071,437 A | 12/1991 | Steffee |
| 5,258,098 A | 11/1993 | Wagner et al. |
| 5,306,308 A | 4/1994 | Gross et al. |
| 5,306,309 A | 4/1994 | Wagner et al. |
| 5,425,772 A | 6/1995 | Brantigan |
| 5,443,514 A | 8/1995 | Steffee |
| 5,456,723 A | 10/1995 | Steinemann et al. |
| 5,507,815 A | 4/1996 | Wagner et al. |
| 5,571,188 A | 11/1996 | Ellingsen et al. |
| 5,603,338 A * | 2/1997 | Beaty ............... A61C 8/00 128/898 |
| 5,609,635 A | 3/1997 | Michelson |
| 5,702,449 A | 12/1997 | McKay |
| 5,755,798 A | 5/1998 | Papavero et al. |
| 5,766,252 A | 6/1998 | Henry et al. |
| 5,776,199 A | 7/1998 | Michelson |
| 5,860,973 A | 1/1999 | Michelson |
| 5,863,201 A | 1/1999 | Lazzara et al. |
| 5,865,845 A | 2/1999 | Thalgott |
| 5,876,453 A * | 3/1999 | Beaty ............... A61C 8/00 433/201.1 |
| 5,885,079 A | 3/1999 | Niznick |
| 5,888,224 A | 3/1999 | Beckers et al. |
| 5,922,029 A | 7/1999 | Wagner et al. |
| 5,968,098 A | 10/1999 | Winslow |
| 5,984,922 A | 11/1999 | McKay |
| 6,033,582 A | 3/2000 | Lee et al. |
| 6,039,762 A | 3/2000 | McKay |
| 6,059,829 A | 5/2000 | Schlaepfer et al. |
| 6,080,158 A | 6/2000 | Lin |
| 6,086,613 A | 7/2000 | Camino et al. |
| 6,096,107 A | 8/2000 | Caracostas et al. |
| 6,123,705 A | 9/2000 | Michelson |
| 6,143,032 A | 11/2000 | Schafer et al. |
| 6,176,882 B1 | 1/2001 | Biedermann et al. |
| 6,183,255 B1 | 2/2001 | Oshida |
| 6,193,757 B1 | 2/2001 | Foley et al. |
| 6,193,762 B1 | 2/2001 | Wagner et al. |
| 6,241,770 B1 | 6/2001 | Michelson |
| 6,241,771 B1 | 6/2001 | Gresser et al. |
| 6,245,108 B1 * | 6/2001 | Biscup ............... 623/17.11 |
| 6,296,664 B1 | 10/2001 | Middleton |
| 6,302,914 B1 | 10/2001 | Michelson |
| 6,325,827 B1 * | 12/2001 | Lin ............... 623/17.16 |
| 6,342,074 B1 * | 1/2002 | Simpson ............... 623/17.11 |
| 6,344,057 B1 | 2/2002 | Rabbe et al. |
| 6,350,283 B1 | 2/2002 | Michelson |
| 6,375,681 B1 | 4/2002 | Truscott |
| 6,387,130 B1 | 5/2002 | Stone et al. |
| 6,395,031 B1 | 5/2002 | Foley et al. |
| 6,423,095 B1 | 7/2002 | Van Hoeck et al. |
| 6,425,920 B1 | 7/2002 | Hamada |
| 6,432,140 B1 | 8/2002 | Lin |
| 6,436,102 B1 | 8/2002 | Ralph et al. |
| 6,447,544 B1 | 9/2002 | Michelson |
| 6,458,159 B1 | 10/2002 | Thalgott |
| 6,478,823 B1 | 11/2002 | Michelson |
| 6,482,233 B1 * | 11/2002 | Aebi ............... A61F 2/4465 623/17.11 |
| 6,485,517 B1 | 11/2002 | Michelson |
| 6,491,723 B1 | 12/2002 | Beaty |
| 6,520,993 B2 | 2/2003 | James et al. |
| 6,558,424 B2 | 5/2003 | Thalgott |
| 6,569,201 B2 | 5/2003 | Moumene et al. |
| 6,579,318 B2 | 6/2003 | Varga et al. |
| 6,592,624 B1 | 7/2003 | Fraser et al. |
| 6,599,322 B1 | 7/2003 | Amrich et al. |
| 6,610,089 B1 | 8/2003 | Liu et al. |
| 6,620,332 B2 | 9/2003 | Amrich |
| 6,635,086 B2 | 10/2003 | Lin |
| 6,652,765 B1 | 11/2003 | Beaty |
| 6,676,703 B2 | 1/2004 | Biscup |
| 6,702,855 B1 | 3/2004 | Steinemann et al. |
| 6,719,794 B2 | 4/2004 | Gerber et al. |
| 6,726,720 B2 | 4/2004 | Ross et al. |
| 6,730,127 B2 | 5/2004 | Michelson |
| 6,740,118 B2 | 5/2004 | Eisermann et al. |
| 6,743,231 B1 | 6/2004 | Gray et al. |
| 6,758,849 B1 | 7/2004 | Michelson |
| 6,833,006 B2 | 12/2004 | Foley et al. |
| 6,890,355 B2 | 5/2005 | Michelson |
| 6,902,581 B2 | 6/2005 | Walkenhorst et al. |
| 6,911,249 B2 | 6/2005 | Wagner et al. |
| 6,923,810 B1 | 8/2005 | Michelson |
| 6,964,687 B1 * | 11/2005 | Bernard et al. ............. 623/17.16 |
| 6,974,480 B2 | 12/2005 | Messerli et al. |
| 6,981,975 B2 | 1/2006 | Michelson |
| 7,018,412 B2 | 3/2006 | Ferreira et al. |
| 7,018,418 B2 | 3/2006 | Amrich et al. |
| 7,041,137 B2 | 5/2006 | Fulton et al. |
| 7,044,972 B2 | 5/2006 | Mathys, Jr. et al. |
| 7,048,870 B1 | 5/2006 | Ellingsen et al. |
| 7,060,073 B2 | 6/2006 | Frey et al. |
| 7,066,961 B2 | 6/2006 | Michelson |
| 7,077,864 B2 | 7/2006 | Byrd, III et al. |
| 7,087,085 B2 | 8/2006 | Steinemann et al. |
| 7,112,224 B2 | 9/2006 | Lie et al. |
| 7,128,760 B2 | 10/2006 | Michelson |
| 7,137,997 B2 | 11/2006 | Paul |
| 7,141,068 B2 | 11/2006 | Ross et al. |
| 7,144,428 B2 | 12/2006 | Anitua |
| 7,166,129 B2 | 1/2007 | Michelson |
| 7,169,183 B2 | 1/2007 | Liu et al. |
| D539,934 S | 4/2007 | Blain |

(56) References Cited

U.S. PATENT DOCUMENTS

| | | | |
|---|---|---|---|
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 | 5/2007 | Trieu et al. | |
| 7,226,480 B2 | 6/2007 | Thalgott | |
| 7,238,186 B2 | 7/2007 | Zdeblick et al. | |
| 7,244,275 B2 | 7/2007 | Michelson | |
| 7,250,060 B2 | 7/2007 | Trieu | |
| 7,255,698 B2 | 8/2007 | Michelson | |
| 7,288,093 B2 | 10/2007 | Michelson | |
| 7,311,734 B2 | 12/2007 | Van Hoeck et al. | |
| D564,095 S | 3/2008 | Blain | |
| 7,347,873 B2 | 3/2008 | Paul et al. | |
| D566,276 S | 4/2008 | Blain | |
| 7,368,065 B2 | 5/2008 | Yang et al. | |
| 7,410,501 B2 | 8/2008 | Michelson | |
| 7,501,073 B2 | 3/2009 | Wen et al. | |
| 7,503,933 B2 | 3/2009 | Michelson | |
| 7,517,363 B2 | 4/2009 | Rogers et al. | |
| D599,019 S | 8/2009 | Pimenta et al. | |
| 7,569,074 B2 | 8/2009 | Eisermann et al. | |
| 7,608,107 B2 | 10/2009 | Michelson | |
| 7,615,078 B2 | 11/2009 | White et al. | |
| 7,655,042 B2 | 2/2010 | Foley et al. | |
| 7,662,186 B2 | 2/2010 | Bagga et al. | |
| 7,662,190 B2 | 2/2010 | Steinemann et al. | |
| 7,744,612 B2 | 6/2010 | Blain | |
| 7,846,183 B2 | 12/2010 | Blain | |
| 7,901,462 B2 | 3/2011 | Yang et al. | |
| 7,998,172 B2 | 8/2011 | Blain | |
| 8,062,304 B2 | 11/2011 | Blain et al. | |
| 8,100,955 B2 | 1/2012 | Blain et al. | |
| 8,142,355 B2 | 3/2012 | Blain et al. | |
| 8,157,864 B2 | 4/2012 | Rogeau et al. | |
| 8,172,854 B2 | 5/2012 | Blain et al. | |
| 8,262,737 B2 | 9/2012 | Bagga et al. | |
| 2001/0014826 A1 | 8/2001 | Biedermann et al. | |
| 2001/0016777 A1 | 8/2001 | Biscup | |
| 2001/0039464 A1 | 11/2001 | Ricci et al. | |
| 2001/0047208 A1 | 11/2001 | Michelson | |
| 2002/0049497 A1 | 4/2002 | Mason | |
| 2002/0087212 A1 | 7/2002 | James et al. | |
| 2002/0099443 A1 | 7/2002 | Messerli et al. | |
| 2002/0128716 A1 | 9/2002 | Cohen et al. | |
| 2002/0138142 A1 | 9/2002 | Castro et al. | |
| 2002/0156529 A1* | 10/2002 | Li et al. | 623/17.11 |
| 2002/0161443 A1 | 10/2002 | Michelson | |
| 2002/0173854 A1 | 11/2002 | Amrich | |
| 2002/0188294 A1 | 12/2002 | Couture et al. | |
| 2003/0014116 A1 | 1/2003 | Ralph et al. | |
| 2003/0083668 A1 | 5/2003 | Rogers et al. | |
| 2003/0105527 A1 | 6/2003 | Bresina | |
| 2003/0109928 A1 | 6/2003 | Pasquet et al. | |
| 2003/0125739 A1* | 7/2003 | Bagga et al. | 606/61 |
| 2003/0153975 A1* | 8/2003 | Byrd, III | A61F 2/447 623/17.11 |
| 2003/0176925 A1 | 9/2003 | Paponneau | |
| 2003/0181980 A1 | 9/2003 | Berry et al. | |
| 2003/0181981 A1 | 9/2003 | Lemaire | |
| 2003/0187506 A1 | 10/2003 | Ross et al. | |
| 2003/0191531 A1 | 10/2003 | Berry et al. | |
| 2004/0073314 A1 | 4/2004 | White et al. | |
| 2004/0117019 A1 | 6/2004 | Trieu et al. | |
| 2004/0117020 A1 | 6/2004 | Frey et al. | |
| 2004/0122518 A1* | 6/2004 | Rhoda | 623/17.11 |
| 2004/0127993 A1 | 7/2004 | Kast et al. | |
| 2004/0134886 A1 | 7/2004 | Wagner et al. | |
| 2004/0153154 A1 | 8/2004 | Dinkelacker | |
| 2004/0153160 A1 | 8/2004 | Carrasco | |
| 2004/0162616 A1 | 8/2004 | Simonton et al. | |
| 2004/0167632 A1 | 8/2004 | Wen et al. | |
| 2004/0210309 A1 | 10/2004 | Denzer et al. | |
| 2004/0230306 A1 | 11/2004 | Hoeck et al. | |
| 2004/0265780 A1 | 12/2004 | Robb et al. | |
| 2004/0267367 A1 | 12/2004 | O'Neil | |
| 2005/0021150 A1 | 1/2005 | Michelson | |
| 2005/0027360 A1 | 2/2005 | Webb et al. | |
| 2005/0038512 A1 | 2/2005 | Michelson | |
| 2005/0060034 A1 | 3/2005 | Berry et al. | |
| 2005/0075734 A1 | 4/2005 | Fulton et al. | |
| 2005/0085913 A1 | 4/2005 | Fraser et al. | |
| 2005/0119758 A1* | 6/2005 | Alexander et al. | 623/23.5 |
| 2005/0131416 A1 | 6/2005 | Jansen et al. | |
| 2005/0147942 A1 | 7/2005 | Hall | |
| 2005/0159814 A1 | 7/2005 | Karahalios | |
| 2005/0161120 A1 | 7/2005 | Inagaki et al. | |
| 2005/0165483 A1 | 7/2005 | Ray et al. | |
| 2005/0203630 A1 | 9/2005 | Pope et al. | |
| 2005/0251257 A1 | 11/2005 | Mitchell et al. | |
| 2006/0025860 A1* | 2/2006 | Li | 623/17.11 |
| 2006/0030943 A1 | 2/2006 | Peterman | |
| 2006/0041313 A1 | 2/2006 | Allard et al. | |
| 2006/0093646 A1 | 5/2006 | Cima et al. | |
| 2006/0100705 A1* | 5/2006 | Puno | A61F 2/30771 623/17.11 |
| 2006/0149372 A1 | 7/2006 | Paxson et al. | |
| 2006/0149376 A1 | 7/2006 | Shimp et al. | |
| 2006/0167549 A1 | 7/2006 | Mathys, Jr. et al. | |
| 2006/0190079 A1 | 8/2006 | Istephanous et al. | |
| 2006/0219661 A1 | 10/2006 | Towse et al. | |
| 2006/0235534 A1 | 10/2006 | Gertzman et al. | |
| 2006/0265065 A1 | 11/2006 | Bagga et al. | |
| 2006/0293748 A1* | 12/2006 | Alexander et al. | 623/17.11 |
| 2007/0010885 A1 | 1/2007 | Liu et al. | |
| 2007/0093898 A1 | 4/2007 | Schwab et al. | |
| 2007/0118220 A1 | 5/2007 | Liu et al. | |
| 2007/0118223 A1 | 5/2007 | Allard et al. | |
| 2007/0173938 A1* | 7/2007 | Sweeney | 623/17.11 |
| 2007/0208343 A1* | 9/2007 | Magerl et al. | 606/61 |
| 2007/0213826 A1* | 9/2007 | Smith et al. | 623/17.11 |
| 2007/0213832 A1* | 9/2007 | Wen | 623/23.5 |
| 2007/0225810 A1* | 9/2007 | Colleran | A61F 2/442 623/17.13 |
| 2007/0233247 A1 | 10/2007 | Schwab | |
| 2007/0233248 A1 | 10/2007 | Schwab et al. | |
| 2007/0260320 A1 | 11/2007 | Peterman et al. | |
| 2007/0269475 A1 | 11/2007 | Gil et al. | |
| 2007/0270839 A1 | 11/2007 | Jeon et al. | |
| 2007/0270951 A1 | 11/2007 | Davis et al. | |
| 2007/0270956 A1 | 11/2007 | Heinz | |
| 2007/0276492 A1* | 11/2007 | Andrews | A61F 2/442 623/17.11 |
| 2007/0282441 A1 | 12/2007 | Stream et al. | |
| 2007/0288028 A1 | 12/2007 | Gorensek et al. | |
| 2007/0293949 A1 | 12/2007 | Salerni et al. | |
| 2008/0014243 A1 | 1/2008 | Ellingsen et al. | |
| 2008/0071380 A1 | 3/2008 | Sweeney | |
| 2008/0077171 A1 | 3/2008 | Blain et al. | |
| 2008/0097610 A1 | 4/2008 | Guyer et al. | |
| 2008/0109081 A1* | 5/2008 | Bao et al. | 623/17.15 |
| 2008/0154378 A1 | 6/2008 | Pelo | |
| 2008/0195209 A1 | 8/2008 | Garcia et al. | |
| 2008/0221689 A1 | 9/2008 | Chaput et al. | |
| 2008/0249622 A1 | 10/2008 | Gray | |
| 2008/0262623 A1* | 10/2008 | Bagga | A61F 2/442 623/17.16 |
| 2008/0269764 A1 | 10/2008 | Blain et al. | |
| 2008/0269806 A1 | 10/2008 | Zhang et al. | |
| 2008/0288076 A1 | 11/2008 | Soo et al. | |
| 2009/0005784 A1 | 1/2009 | Blain et al. | |
| 2009/0005871 A1 | 1/2009 | White et al. | |
| 2009/0014243 A1 | 1/2009 | Whigham | |
| 2009/0024132 A1 | 1/2009 | Blain et al. | |
| 2009/0082819 A1 | 3/2009 | Blain et al. | |
| 2009/0088800 A1 | 4/2009 | Blain et al. | |
| 2009/0088853 A1 | 4/2009 | Ogilvie et al. | |
| 2009/0132048 A1 | 5/2009 | Denzer | |
| 2009/0182377 A1 | 7/2009 | Petersen | |
| 2009/0182432 A1 | 7/2009 | Zdeblick et al. | |
| 2009/0187247 A1 | 7/2009 | Metcalf, Jr. et al. | |
| 2009/0204152 A1 | 8/2009 | Blain | |
| 2009/0234362 A1 | 9/2009 | Blain et al. | |
| 2009/0264928 A1 | 10/2009 | Blain | |
| 2009/0276049 A1 | 11/2009 | Weiland | |

(56) References Cited

U.S. PATENT DOCUMENTS

| | | |
|---|---|---|
| 2009/0312837 A1 | 12/2009 | Eisermann et al. |
| 2010/0173264 A1 | 1/2010 | Fredriksson et al. |
| 2010/0057206 A1* | 3/2010 | Duffield .................. A61F 2/447 623/17.16 |
| 2010/0076559 A1 | 3/2010 | Bagga et al. |
| 2010/0094426 A1* | 4/2010 | Grohowski et al. ....... 623/17.16 |
| 2010/0121385 A1 | 5/2010 | Blain et al. |
| 2010/0168798 A1* | 7/2010 | Clineff et al. ................ 606/279 |
| 2010/0204798 A1 | 8/2010 | Gerbec et al. |
| 2010/0218854 A1* | 9/2010 | Garcia Saban ......... A61L 27/06 148/269 |
| 2010/0228288 A1 | 9/2010 | Blain |
| 2010/0249937 A1 | 9/2010 | Blain et al. |
| 2010/0274286 A1 | 10/2010 | Blain et al. |
| 2010/0274358 A1 | 10/2010 | Mueller et al. |
| 2010/0303722 A1 | 12/2010 | Jin et al. |
| 2011/0009965 A1* | 1/2011 | Ankem ...................... 623/17.11 |
| 2011/0040301 A1 | 2/2011 | Blain et al. |
| 2011/0082503 A1 | 4/2011 | Blain |
| 2011/0190888 A1* | 8/2011 | Bertele et al. ............. 623/17.11 |
| 2011/0190902 A1 | 8/2011 | Tong et al. |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1* | 11/2011 | Ullrich, Jr. ............. A61F 2/4465 623/17.16 |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ullrich, Jr. et al. |
| 2012/0239150 A1 | 9/2012 | Ullrich, Jr. et al. |
| 2012/0239151 A1 | 9/2012 | Ullrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |
| 2013/0248487 A1* | 9/2013 | Mayfield ............... A61C 13/225 216/53 |

FOREIGN PATENT DOCUMENTS

| | | |
|---|---|---|
| EP | 1440669 B1 | 7/2004 |
| EP | 1449544 | 8/2004 |
| EP | 2 386 274 A1 | 11/2011 |
| JP | 08-010276 A | 1/1996 |
| JP | 2001170092 A | 6/2001 |
| WO | 1997/06753 A2 | 2/1997 |
| WO | 98/01091 | 1/1998 |
| WO | 0128469 | 4/2001 |
| WO | 2001/70144 A1 | 9/2001 |
| WO | 2001/95838 A1 | 12/2001 |
| WO | 2004008983 | 1/2004 |
| WO | 2004041131 | 5/2004 |
| WO | 2006/081843 A1 | 8/2006 |
| WO | 2006/116306 A2 | 11/2006 |
| WO | 2006/119088 A2 | 11/2006 |
| WO | 2006121795 | 11/2006 |
| WO | 2007/089905 A2 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2010/010536 A1 | 1/2010 |
| WO | 2010010536 | 1/2010 |
| WO | 2011094748 | 8/2011 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of $TiO_2$ grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/ Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growith of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report dated Sep. 27, 2011.

Supplementary Partial European Search Report dated Aug. 19, 2011.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

Wennerberg, A., et al., "Effects of titanium surface topography on bone integration: a systematic review", Clin. Oral Impl. Res., 20 (Suppl. 4), 2009, pp. 172-184.

Pending U.S. Appl. No. 13/286,813 of Chad J. Patterson, et al. filed Nov. 1, 2011.

Pending U.S. Appl. No. 13/826,304 of Peter F. Ullrich, Jr., et al. filed Mar. 14, 2013.

Pending U.S. Appl. No. 13/713,417 of Chad J. Patterson, et al. filed Dec. 13, 2012.

International Search Report and Written Opinion of the International Searching Authority, dated Oct. 24, 2014, of International Application No. PCT/US2013/050818.

* cited by examiner

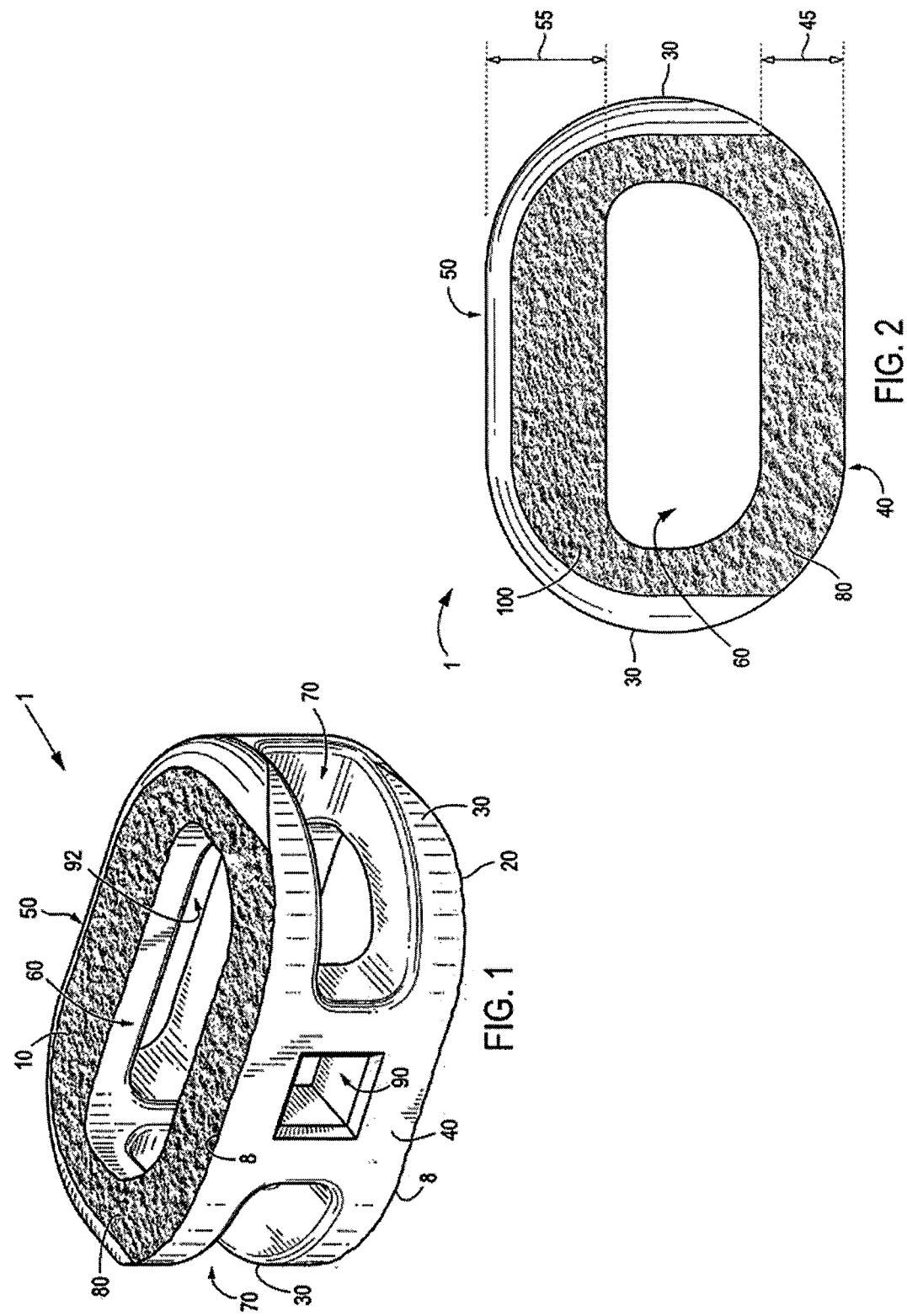

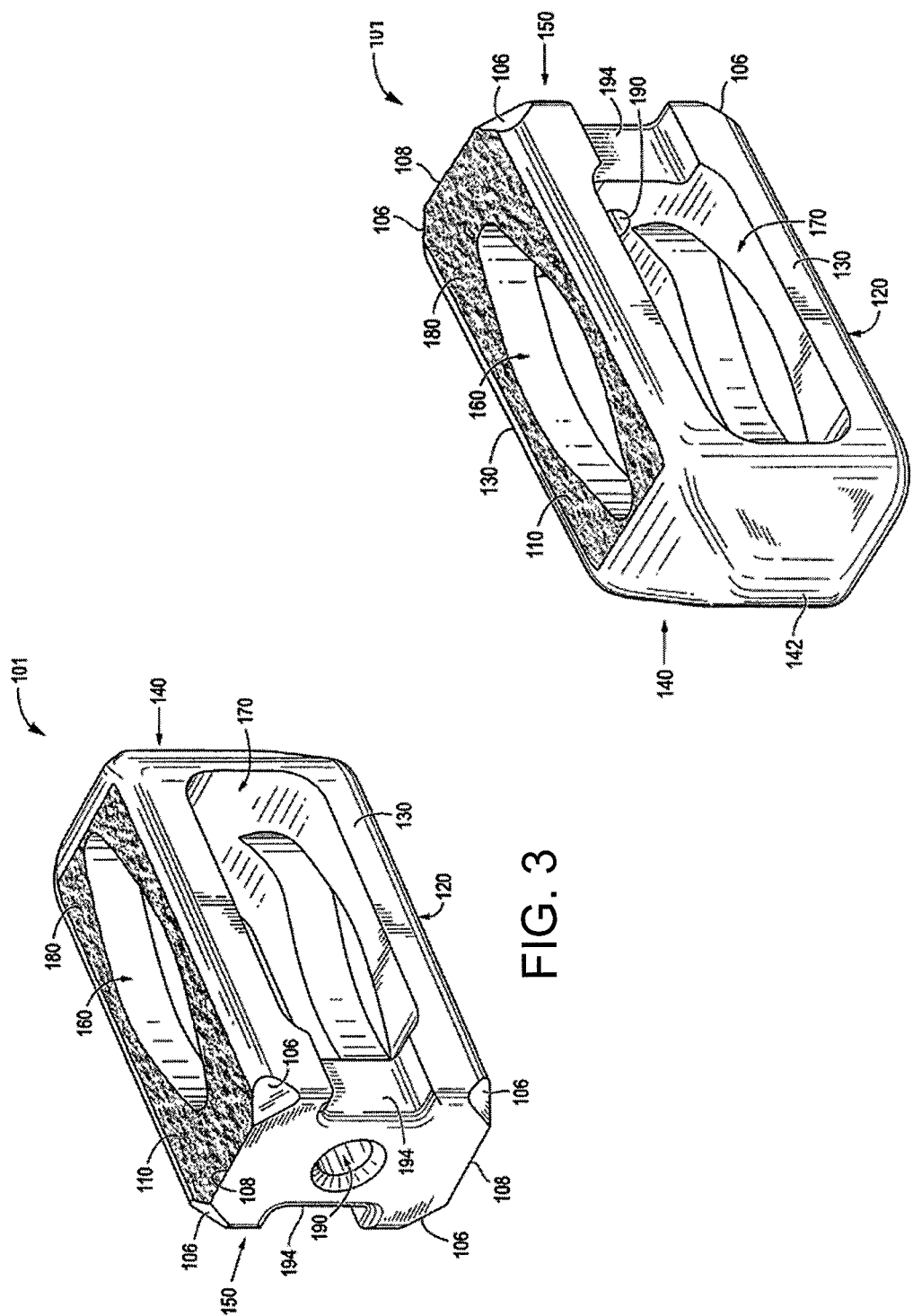

INTERBODY SPINAL IMPLANT HAVING A ROUGHENED SURFACE TOPOGRAPHY ON ONE OR MORE INTERNAL SURFACES

CROSS REFERENCE TO RELATED APPLICATIONS

This application is a continuation-in-part of U.S. application Ser. No. 13/572,077, which was filed on Aug. 10, 2012 and issued as U.S. Pat. No. 8,496,710 on Jul. 30, 2013 as a continuation of U.S. application Ser. No. 12/151,198, which was filed on May 5, 2008 and issued as U.S. Pat. No. 8,262,737 on Sep. 11, 2012, which is a continuation-in-part of U.S. application Ser. No. 11/123,359, which was filed on May 6, 2005 and issued as U.S. Pat. No. 7,662,186 on Feb. 16, 2010, and is a continuation-in-part of U.S. application Ser. No. 13/107,886, which was filed on May 14, 2011 and later abandoned and claims priority to U.S. Provisional Application No. 61/334,853, which was filed on May 14, 2010, the contents of each are incorporated by reference herein, in their entirety and for all purposes.

FIELD OF THE INVENTION

The invention relates generally to interbody spinal implants, and in particular, to spinal implants comprising one or more vertical and transverse apertures that intersect a substantially hollow center, with the surfaces of one or more of these apertures and/or the surfaces of the hollow center comprising a roughened surface topography, which facilitates integration of the implant with newly formed bone when the implant is implanted into the spine of a patient.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, develop deformities such as tears/cracks, or simply lose structural integrity, for example bulge or flatten. These impaired discs can affect the anatomical functions of the vertebrae, due to the resultant lack of proper biomechanical support, and are often associated with chronic back pain.

Several surgical techniques have been developed to address spinal defects, such as disc degeneration, deformity, or both. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or anterior approach. Anterior interbody fusion procedures generally have reduced operative times, reduced blood loss, and do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

An implant system's corresponding surgical procedure should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Traditional interbody spinal implants generally do not seat properly on the preferred structural bone located near the apophyseal rim of the vertebral body, which is primarily composed of preferred dense subchondral bone. To address this problem, surface geometries and textures may be varied to promote proper seating of the implant. For example, the top and bottom surfaces may have texturing or features to improve load transferring surface area, engage bone structures and resist movement under loads imparted by patient activity. In addition to large features and shapes, the surfaces may also have microscopic features and shapes intended to aid in the biologic attachment of the vertebrae by biologically interacting with the bone cells. Most of these implants also have internal passages for the placement of graft and bone growth enhancing materials inside of the implant intended to aid in the formation of a stable fusion. This graft material forms part of the fusion that is intended to form with the disc space of the patient by providing biologically compatible material, often including patient-derived or synthesized biologic materials. Graft materials are intended to be remodeled and/or absorbed during the healing phases and the stability of the implant and graft materials is critical to the successful formation of new bone tissues and long term fusion stability. One problem with certain implants, however, is that they do not promote bone growth into the graft material in the internal passage of the implant. Accordingly, there is a need for interbody spinal implants that better utilize the graft materials and promotes bone growth in the internal passages of the implants.

SUMMARY OF THE INVENTION

The invention features interbody spinal implants. The implants generally comprise a body comprising a top surface, a bottom surface, opposing lateral sides, opposing anterior and posterior portions, internal sidewalls around a substantially hollow center, and a single vertical aperture extending from the top surface to the bottom surface, having maximum width at its center, and defining a transverse rim on the top surface and on the bottom surface that has a posterior thickness greater than an anterior thickness or that has an anterior thickness greater than a posterior thickness. The transverse rim has a blunt and radiused portion along the top of each lateral side, and along the top of the posterior portion and/or along the top of the anterior portion. The portion of the transverse rim that is not blunt and radiused, and at least a portion of the internal sidewalls have a roughened surface topography, and the blunt and radiused portion does not include any roughened surface topography.

The body may comprise a generally oval-shaped transverse cross section, a generally rectangular transverse cross section, or a generally curved transverse cross section. The body is preferably comprised of titanium or an alloy thereof. In some aspects, the body comprises at least one transverse aperture through each of the opposing lateral sides, and the sidewalls of the transverse aperture comprise roughened surface topography. Two, three, four, five, six, seven, eight, or more transverse apertures may be present. The transverse aperture may comprise an intermediate wall. The body may comprise a rear wall.

Internal sidewalls that comprise roughened surface topography may include one or any combination of the sidewalls of the vertical aperture, the sidewalls of the transverse aperture(s), the internal surface of the intermediate wall, the rear wall, and other walls of the interior of the body that surround and/or define the substantially hollow center. The implant may comprise a bone graft material disposed in the substantially hollow center, and this bone graft material preferably is in contact with the roughened surface topography of the internal surfaces.

The roughened surface topography may comprise macro features comprising an amplitude of about 20 microns to about 200 microns from the peak to the mean line and a peak-to-valley height of about 40 microns to about 500 microns, and a spacing of about 400 microns to about 2000 microns between macro features. The roughened surface topography may comprise micro features comprising an amplitude of about 1 micron to about 20 microns from the peak to the mean line and a peak-to-valley height of about 2 microns to about 40 microns, and a spacing of about 20 microns to about 400 microns between micro features. The roughened surface topography may comprise nano features comprising an amplitude of about 0.01 microns to about 1 micron from the peak to the mean line and a peak-to-valley height of about 0.2 microns to about 2 microns, and a spacing of about 0.5 microns to about 20 microns between nano features.

BRIEF DESCRIPTION OF THE DRAWINGS

FIG. 1 shows a perspective view of an embodiment of the interbody spinal implant having a generally oval shape and roughened surface topography on the top surface;

FIG. 2 shows a top view of the first embodiment of the interbody spinal implant illustrated in FIG. 1;

FIG. 3 shows a perspective view from the front of another embodiment of the interbody spinal implant according to the invention;

FIG. 4 shows a perspective view from the rear of the embodiment of the interbody spinal implant illustrated in FIG. 3;

DETAILED DESCRIPTION OF THE INVENTION

Figure 5:
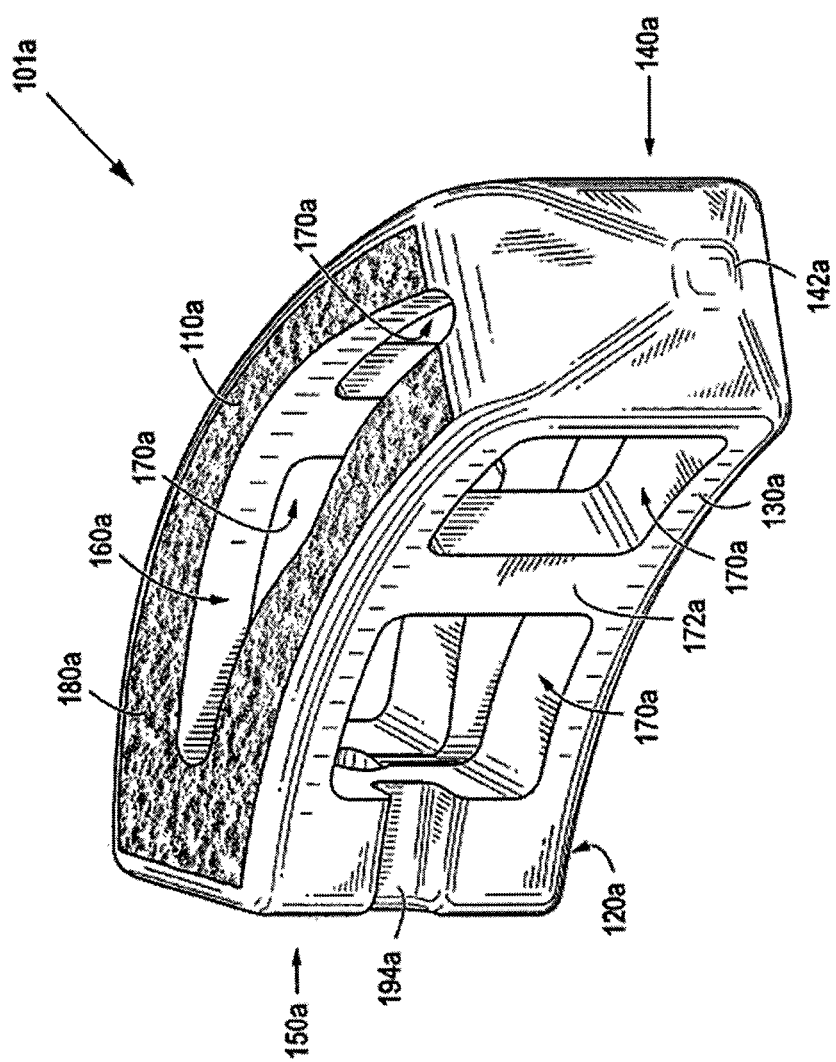
FIG. 5 shows a perspective view of another embodiment of the interbody spinal implant according to the invention, including a transverse aperture.

Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the invention, allow for improved visualization of implant seating and fusion assessment. Interbody spinal implants, as now taught, may also facilitate osteointegration with the surrounding living bone.

Anterior interbody spinal implants in accordance with certain aspects of the invention can be preferably made of a durable material such as stainless steel, stainless steel alloy, titanium, or titanium alloy, but can also be made of other durable materials such as, but not limited to, polymeric, ceramic, and composite materials. For example, certain embodiments of the invention may be comprised of a biocompatible, polymeric matrix reinforced with bioactive fillers, fibers, or both. Certain embodiments of the invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor during implantation.

FIG. 1 shows a perspective view of a first embodiment of the interbody spinal implant 1 especially well adapted for use in an ALIF procedure. The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. The roughened topography 80, however, is distinct from the teeth provided on the surfaces of some conventional devices.

In some aspects, the interbody spinal implant 1 is substantially hollow and has a generally oval-shaped transverse cross-sectional area with smooth, rounded, or both smooth and rounded lateral sides 30 and posterior-lateral corners 52. A substantially hollow implant 1 includes an implant 1 having at least about 33% of the interior volume of the implant 1 vacant. The implant 1 includes at least one vertical aperture 60 that extends the entire height of the implant body. As illustrated in the top view of FIG. 2, the vertical aperture 60 may further define a transverse rim 100 having a greater posterior portion thickness 55 than an anterior portion thickness 45.

In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40. Some studies have challenged the characterization of the posterior endplate bone as weaker.

The implant 1 may also have a lordotic angle to facilitate alignment. The anterior side 40 is preferably generally greater in height than the posterior side 50. Therefore, the implant 1 may better compensate for the generally less supportive bone found in certain regions of the vertebral endplate.

The implant 1 may further include at least one transverse aperture 70. Like the vertical aperture 60, the size and shape of the transverse aperture 70 are carefully chosen (and predetermined) to achieve a preferable design tradeoff for the particular application envisioned for the implant 1. Specifically, the transverse aperture 70 should have minimal dimensions to maximize the strength and structural integrity of the implant 1. On the other hand, the transverse aperture 70 should have maximum dimensions to (a) improve the visibility of the implant 1 during surgical procedures to ensure proper implant placement and seating, and to improve post-operative assessment of implant fusion, and (b) to facilitate engagement between bone graft material and adjacent bone. The substantially hollow area defined by the implant 1 may be filled with bone graft materials to facilitate the formation of a solid fusion column within the spine of a patient.

As noted above, FIG. 1 shows a perspective view of one embodiment of the invention, the interbody spinal implant 1, which is especially well adapted for use in an ALIF procedure. Other embodiments of the invention are better suited for PLIF, TLIF, or cervical fusion procedures. Specifically, FIGS. 3 and 4 show perspective views of an embodiment of an interbody spinal implant 101 especially well adapted for use in a PLIF procedure. The interbody spinal implant 101 includes a body having a top surface 110, a bottom surface 120, opposing lateral sides 130, and opposing anterior 140 and posterior 150 portions. One or both of the top surface 110 and the bottom surface 120 has a roughened topography 180 for gripping adjacent bone and inhibiting migration of the implant 101.

Certain embodiments of the interbody spinal implant 101 are substantially hollow and have a generally rectangular shape with smooth, rounded, or both smooth and rounded lateral sides and anterior-lateral corners. As shown in FIG. 4, the anterior portion 140 may have a tapered nose 142 to facilitate insertion of the implant 101. To further facilitate insertion, the implant 101 has chamfers 106 at the corners of its posterior portion 150. The chamfers 106 prevent the implant 101 from catching upon insertion, risking potential damage such as severed nerves, while still permitting the implant 101 to have an anti-expulsion edge 108.

The implant 101 includes at least one vertical aperture 160 that extends the entire height of the implant body. The vertical aperture 160 further defines a transverse rim 200. The size and shape of the vertical aperture 160 are carefully chosen to achieve a preferable design tradeoff for the particular application envisioned for the implant 101. Specifically, the vertical aperture 160 seeks to maximize the surface area of the top surface 110 and the bottom surface 120 available proximate the anterior 140 and posterior 150 portions while maximizing both radiographic visualization and access to the bone graft material toward the center of the top 110 and bottom 120 surfaces. Thus, the size and shape of the vertical aperture 160 are predetermined by the application to which the implant 101 will be used.

In the particular example shown in FIGS. 3 and 4, the width of the implant 101 between the two lateral sides 130 is approximately 9 mm. The shape of the vertical aperture 160 approximates, in cross section, that of an American football. The center of the vertical aperture 160, which defines the maximum width of the vertical aperture 160, is about 5 mm. Thus, the rim thickness 200 on either side of the vertical aperture 160 adjacent the center of the vertical aperture 160 is about 2 mm. These dimensions permit ample engagement between the bone graft material contained within the implant 101 and bone.

The vertical aperture 160 tapers from its center to its ends along a longitudinal distance of about 7.75 mm (thus, the total length of the vertical aperture 160 is about 15.5 mm). This shape leaves intact much of the rim thickness 200 in the areas around the ends of the vertical aperture 160. These areas may allow for better stress sharing between the implant 101 and the adjacent vertebral endplates. Thus, the transverse rim 200 has a generally large surface area and contacts the vertebral endplate.

As illustrated in FIG. 3, the implant 101 has an opening 190 in the posterior portion 150. The opening 190 has a number of functions. One function is to facilitate manipulation of the implant 101 by the caretaker. Thus, the caretaker may insert a surgical tool into the opening 190 and, through the engagement between the surgical tool and the opening 190, manipulate the implant 101. The opening 190 may be threaded to enhance the engagement.

The implant 101 may also have an Implant Holding Feature (IHF) 194 instead of or in addition to the opening 190. As illustrated in FIG. 3, the IHF 194 is located proximate the opening 190 in the posterior portion 150. In this particular example, the IHF 194 is a U-shaped notch. Like the opening 190, the IHF 194 has a number of functions, one of which is to facilitate manipulation of the implant 101 by the caretaker. Other functions of the opening 190 and the IHF 194 are to increase visibility of the implant 101 during surgical procedures and to enhance engagement between bone graft material and adjacent bone.

The implant 101 may further include at least one transverse aperture 170. Like the vertical aperture 160, the size and shape of the transverse aperture 170 are carefully chosen (and predetermined) to achieve a preferable design tradeoff for the particular application envisioned for the implant 101. Specifically, the transverse aperture 170 should have minimal dimensions to maximize the strength and structural integrity of the implant 101. On the other hand, the transverse aperture 170 should have maximum dimensions to (a) improve the visibility of the implant 101 during surgical procedures to ensure proper implant placement and seating, and to improve post-operative assessment of implant fusion, and (b) to facilitate engagement between bone graft material and adjacent bone. The substantially hollow area defined by the implant 101 may be filled with bone graft materials to facilitate the formation of a solid fusion column within the spine of a patient.

As shown in FIGS. 3 and 4, the transverse aperture 170 extends the entire transverse length of the implant body and nearly the entire height of the implant body. Thus, the size and shape of the transverse aperture 170 approach the maximum possible dimensions for the transverse aperture 170.

The transverse aperture 170 may be broken into two, separate sections by an intermediate wall 172. The section of the transverse aperture 170 proximate the IHF 194 is substantially rectangular in shape; the other section of the transverse aperture 170 has the shape of a curved arch. Other shapes and dimensions are suitable for the transverse aperture 170. In particular, all edges of the transverse aperture 170 may be rounded, smooth, or both. The intermediate wall 172 may be made of the same material as the remainder of the implant 101 (e.g., metal), or it may be made of another material (e.g., PEEK) to form a composite implant 101. The intermediate wall 172 may offer one or more of several advantages, including reinforcement of the implant 101 and improved bone graft containment.

The embodiment of the invention illustrated in FIGS. 3 and 4 is especially well suited for a PLIF surgical procedure. TLIF surgery is done through the posterior (rear) part of the spine and is essentially like an extended PLIF procedure. The TLIF procedure was developed in response to some of the technical problems encountered with a PLIF procedure. The main difference between the two spine fusion procedures is that the TLIF approach to the disc space is expanded by removing one entire facet joint; a PLIF procedure is usually done on both sides by only taking a portion of each of the paired facet joints.

By removing the entire facet joint, visualization into the disc space is improved and more disc material can be removed. Such removal should also provide for less nerve retraction. Because one entire facet is removed, the TLIF procedure is only done on one side: removing the facet joints on both sides of the spine would result in too much instability. With increased visualization and room for dissection, one or both of a larger implant and more bone graft can be used in the TLIF procedure. Theoretically, these advantages can allow the spine surgeon to distract the disc space more and realign the spine better (re-establish the normal lumbar lordosis).

Although the TLIF procedure offers some improvements over a PLIF procedure, the anterior approach in most cases still provides the best visualization, most surface area for healing, and the best reduction of any of the approaches to the disc space. These advantages must be weighed, however, against the increased morbidity (e.g., unwanted aftereffects and postoperative discomfort) of a second incision. Probably the biggest determinate in how the disc space is approached is the comfort level that the spine surgeon has with an anterior approach for the spine fusion surgery. Not all spine surgeons are comfortable with operating around the great vessels (aorta and vena cava) or have access to a skilled vascular surgeon to help them with the approach. Therefore, choosing one of the posterior approaches for the spine fusion surgery is often a more practical solution.

The embodiment of the invention illustrated in FIG. 5 is especially well suited when the spine surgeon elects a TLIF procedure. Many of the features of the implant 101a illustrated in FIG. 5 are the same as those of the implant 101 illustrated in FIGS. 3 and 4. Therefore, these features are given the same reference numbers, with the addition of the letter "a," as those described with respect to implant 101. The interbody spinal implant 101a includes a body having a top surface 110a, a bottom surface 120a, opposing lateral sides 130a, and opposing anterior 140a and posterior 150a portions. One or both of the top surface 110a and the bottom surface 120a has a roughened topography 180a for gripping adjacent bone and inhibiting migration of the implant 101a.

There are several differences, however, between the two embodiments (e.g., implant 101 and implant 101a). For example, unlike the substantially rectangular shape of the implant 101, the implant 101a has a curved shape. Further, the chamfers 106 and anti-expulsion edge 108 of the implant 101 are replaced by curves or rounded edges for the implant 101a. Still further, the TLIF procedure often permits use of a larger implant 101a which, in turn, may affect the size and shape of the predetermined vertical aperture 160a.

The substantially constant 9 mm width of the transverse rim 200 of the implant 101 is replaced with a larger, curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 200) allows the shape of the vertical aperture 160a to change, in cross section, from approximating a football to approximating a boomerang. Maintaining the thickness of the transverse rim 200a on either side of the vertical aperture 160a adjacent the center of the vertical aperture 160a at about 2 mm, similar to the dimensions of the implant 101, the center of the vertical aperture 160a, which defines the maximum width of the vertical aperture 160a, is increased (from 5 mm for the implant 101) to about 7 mm.

The implant 101a may also have a lordotic angle to facilitate alignment. The lateral side 130a depicted at the top of the implant 101a is preferably generally greater in height than the opposing lateral side 130a. Therefore, the implant 101a may better compensate for the generally less supportive bone found in certain regions of the vertebral endplate.

As shown in FIG. 5, the transverse aperture 170a extends the entire transverse length of the implant body and nearly the entire height of the implant body. FIG. 5 also highlights an alternative transverse aperture 170a, where the transverse aperture 170a is broken into two, separate sections by an intermediate wall 172a. Thus, the dimensions of the transverse aperture 170a shown in FIG. 5 are much smaller than those for a single transverse aperture 170a. The two sections of the alternative transverse aperture 170a are each illustrated as substantially rectangular in shape and extending nearly the entire height of the implant body; other sizes and shapes are possible for one or both sections of the alternative transverse aperture 170a.

The intermediate wall 172a may be made of the same material as the remainder of the implant 101a (e.g., metal), or it may be made of another material (e.g., PEEK) to form a composite implant 101a. It is also possible to extend the intermediate wall 172a, whether made of metal, PEEK, ultra-high molecular weight polyethylene (UHMWPE), or another material, to eliminate entirely the transverse aperture 170a. Given the reinforcement function of the intermediate wall 172a, the length of the vertical aperture 160a can be extended (as shown in FIG. 5) beyond the top surface 110a and into the anterior portion 140a of the implant 101a.

The embodiments of the invention described above are best suited for one or more of the ALIF, PLIF, and TLIF surgical procedures. Another embodiment of the invention is better suited for cervical fusion procedures. This embodiment is illustrated in FIGS. 6A and 6B as the interbody spinal implant 201.

Because there is not a lot of disc material between the vertebral bodies in the cervical spine, the discs are usually not very large. The space available for the nerves is also not that great, however, which means that even a small cervical disc herniation may impinge on the nerve and cause significant pain. There is also less mechanical load on the discs in the cervical spine as opposed to the load that exists lower in the spine. Among others, these differences have ramifications for the design of the implant 201.

The implant 201 is generally smaller in size than the other implant embodiments. In addition, the lower mechanical load requirements imposed by the cervical application typically render a composite implant unnecessary. Therefore, the implant 201 is generally made entirely of metal (e.g., titanium) and devoid of other materials (e.g., PEEK).

Figure 6B:
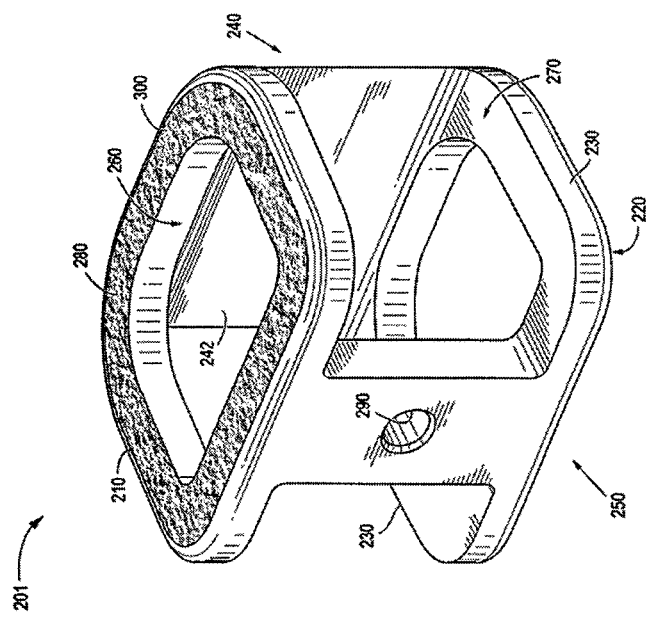
FIG. 6B shows a perspective view of a cervical implant having a generally box shape.
Figure 6A:
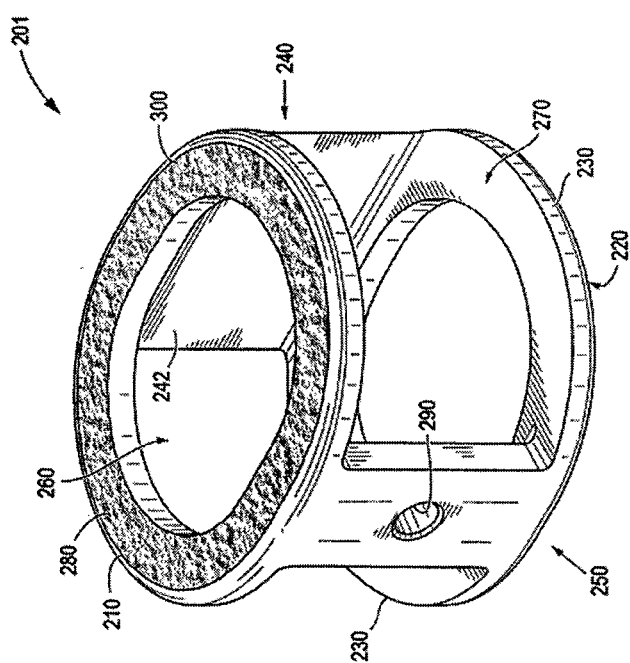
FIG. 6A shows a perspective view of another embodiment of the interbody spinal implant having a generally oval shape and being especially well adapted for use in a cervical spine surgical procedure.

With specific reference to FIG. 6A and FIG. 6B, the implant 201 includes a body having a top surface 210, a bottom surface 220, opposing lateral sides 230, and opposing anterior 240 and posterior 250 portions. One or both of the top surface 210 and the bottom surface 220 has a roughened topography 280 for gripping adjacent bone and inhibiting migration of the implant 201. The implant 201 is substantially hollow and has a generally oval shape with smooth, rounded, or both smooth and rounded edges.

The implant 201 includes at least one vertical aperture 260 that extends the entire height of the implant body. The vertical aperture 260 further defines a transverse rim 300. The size and shape of the vertical aperture 260 are carefully chosen to achieve a preferable design tradeoff for the particular application envisioned for the implant 201. Specifically, the vertical aperture 260 seeks to maximize the surface area of the top surface 210 and the bottom surface 220, to allow for better stress sharing between the implant 201 and the adjacent vertebral endplates, while maximizing access to the bone graft material provided within the implant 201. Thus, the size and shape of the vertical aperture 260 are predetermined by the application.

As illustrated in FIG. 6A, the implant 201 has an opening 290 in the posterior portion 250. The opening 290 has a number of functions. One function is to facilitate manipulation of the implant 201 by the caretaker. Thus, the caretaker may insert a surgical tool into the opening 290 and, through the engagement between the surgical tool and the opening 290, manipulate the implant 201. The opening 290 may be threaded to enhance the engagement.

The implant 201 may further include at least one transverse aperture 270. Like the vertical aperture 260, the size and shape of the transverse aperture 270 are carefully chosen (and predetermined) to achieve a preferable design tradeoff for the particular application envisioned for the implant 201. For example, as shown in FIG. 6A, the transverse aperture 270 may extend the entire transverse length of the implant body and nearly the entire height of the implant body. Thus, the size and shape of the transverse aperture 270 approach the maximum possible dimensions for the transverse aperture 270.

As illustrated in FIG. 6A, the implant 201 may be provided with a solid rear wall 242. The rear wall 242 extends the entire width of the implant body and nearly the entire height of the implant body. Thus, the rear wall 242 essentially closes the anterior portion 240 of the implant 201. The rear wall 242 may offer one or more of several advantages, including reinforcement of the implant 201 and improved bone graft containment. In the cervical application, it may be important to prevent bone graft material from entering the spinal canal.

Alternative shapes for the implant 201 are possible. As illustrated in FIG. 6B, for example, the implant 201 may have a generally box shape which gives the implant 201 increased cortical bone coverage. Like the implant 201 shown in FIG. 6A, the implant 201 shown in FIG. 6B has a curved transverse rim 300 in the area of the anterior portion 240. The shape of the posterior portion 250 of the implant 201 is substantially flat, however, and the shape of the transverse rim 300 in the area of the posterior portion 250 is substantially square. Thus, the posterior portion 250 provides a face that can receive impact from a tool, such as a surgical hammer, to force the implant 201 into position.

The implant 201 may also have a lordotic angle to facilitate alignment. As illustrated in FIGS. 6A and 6B, the anterior portion 240 is preferably generally greater in height than the posterior portion 250. Therefore, the implant 201 may better compensate for the generally less supportive bone found in certain regions of the vertebral endplate. As an example, four degrees of lordosis may be built into the implant 201 to help restore balance to the spine.

Certain embodiments of the implant 1, 101, 101a, and 201 are generally shaped (i.e., made wide) to maximize contact with the apophyseal rim of the vertebral endplates. They are designed to be impacted between the endplates, with fixation to the endplates created by an interference fit and annular tension. Thus, the implants 1, 101, 101a, and 201 are shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis (or more) may be built into the implants 1, 101, 101a, and 201 to help restore cervical balance.

When endplate-sparing spinal implant 1, 101, 101a, and 201 seats in the disc space against the apophyseal rim, it should still allow for deflection of the endplates like a diaphragm. This means that, regardless of the stiffness of the spinal implant 1, 101, 101a, and 201, the bone graft material inside the spinal implant 1, 101, 101a, and 201 receives load, leading to healthy fusion. The vertical load in the human spine is transferred though the peripheral cortex of the vertebral bodies. By implanting an apophyseal-supporting inter-body implant 1, 101, 101a, and 201, the natural biomechanics may be better preserved than for conventional devices.

The vertical aperture 60, 160, 160a, and 260 preferably comprises a maximum width at its center. The width of the vertical aperture 60, 160, 160a, and 260 may range from about 20% to about 80% of the distance between opposing lateral sides. In some aspects, the width ranges from about 40% to about 80% of the distance between the opposing lateral sides. In some aspects, the width ranges from about 50% to about 70% of the distance between the opposing lateral sides. In some aspects, the width ranges from about 50% to about 65% of the distance between the opposing lateral sides. In some aspects, the width ranges from about 60% to about 70% of the distance between the opposing lateral sides. In some aspects, the width ranges from about 55% to about 75% of the distance between the opposing lateral sides. In some aspects, the width ranges from about 60% to about 80% of the distance between the opposing lateral sides. In some aspects, the width is about 40%, about 45%, about 50%, about 55%, about 60%, about 65%, about 70%, about 75%, about 80%, about 85%, or about 90% of the distance between the opposing lateral sides. Preferably, the width of the vertical aperture 60, 160, 160a, and 260 comprises the dimension between the lateral sides.

The length of the vertical aperture 60, 160, 160a, and 260 may range from about 20% to about 80% of the distance between the anterior and posterior edges. In some aspects, the length ranges from about 40% to about 80% of the distance between the anterior and posterior edges. In some aspects, the length ranges from about 50% to about 70% of the distance between the anterior and posterior edges. In some aspects, the length ranges from about 50% to about 65% of the distance between the anterior and posterior edges. In some aspects, the length ranges from about 60% to about 70% of the distance between the anterior and posterior edges. In some aspects, the length ranges from about 55% to about 75% of the distance between the anterior and posterior edges. In some aspects, the length ranges from about 60% to about 80% of the distance between the anterior and posterior edges. In some aspects, the length is about 40%, about 45%, about 50%, about 55%, about 60%, about 65%, about 70%, about 75%, about 80%, about 85%, or about 90% of the distance between the anterior and posterior edges. Preferably, the length of the vertical aperture 60, 160, 160a, and 260 comprises the dimension between the anterior and posterior edges. The size of the length and the size of the width of the vertical aperture 60, 160, 160a, and 260 may vary independently of each other.

It is generally believed that the surface of an implant determines its ultimate ability to integrate into the surrounding living bone. Without being limited to any particular theory or mechanism of action, it is believed that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface. Still further, it appears that these cells attach more readily to relatively rough surfaces rather than smooth surfaces. In this manner, a surface may be bioactive due to its ability to facilitate cellular attachment and osteointegration.

As described above, each implant 1, 101, 101a, and 201 includes a roughened surface topography 80, 180, 180a, and 280, respectively, with this roughened surface topography 80, 180, 180a, and 280 on at least a portion of their top surface 10, 110, 110a, and 210 and/or on at least a portion of their bottom surface 20, 120, 120a, 220. The implant 1, 101, 101a, and 201 preferably comprises a blunt and radiused portion along the top and/or the bottom of each lateral side 30, 130, 130a, and 230, and along the top and/or bottom of the anterior portion 40, 140, 140a, 240, and/or along the top and/or bottom of the posterior portion 50, 150, 150a, and 250. This blunt and radiused portion, generally part of the transverse rim 100, 200, 200a, and 300, preferably does not include any roughened surface topography 80, 180, 180a, and 280. For example, it is preferred that the portions of the top 10, 110, 110a, and 210 and bottom 20, 120, 120a, and 220 surfaces of the implant 1, 101, 101a, and 201 that are not blunt and radiused have the roughened surface topography 80, 180, 180a, and 280. And as discussed in more detail below, such a roughened surface topography 80, 180, 180a, and 280 may be present on additional surfaces, including internal surfaces such as those of the implant hollow center, the vertical aperture 60, 160, 160a, and 260, and/or the transverse aperture 70, 170, 170a, and 270, and/or the opening 90, 190, 190a, and 290.

The roughened surface topography 80, 180, 180a, and 280 may better promote the osteointegration of the implant 1, 101, 101a, and 201. The roughened surface topography 80, 180, 180a, and 280 may also better grip the vertebral endplate surfaces and inhibit migration of the implant 1, 101, 101a, and 201 upon placement and seating in a patient.

The roughened topography 80, 180, 180a, and 280 may be obtained through a variety of techniques including, without limitation, chemical etching, shot peening, plasma etching, laser etching, or abrasive blasting (such as sand or grit blasting). In at least one embodiment, the interbody spinal implant 1, 101, 101a, and 201 may be comprised of titanium, or a titanium alloy, having the surface roughened topography 80, 180, 180a, and 280. The surfaces of the implant 1, 101, 101a, and 201 are preferably bioactive.

In some preferred aspects, the roughened topography 80, 180, 180a, and 280 is obtained via the repetitive masking and chemical or electrochemical milling processes described in U.S. Pat. No. 5,258,098; No. 5,507,815; No. 5,922,029; and No. 6,193,762; each of these patents is incorporated by reference. Where the invention employs chemical etching, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.53 mm. Interbody spinal implants 1, 101, 101a, and 201 in accordance with some preferred embodiments, may be comprised of titanium, or a titanium alloy, having an average surface roughness of about 100 μm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles).

The roughened surface topography 80, 180, 180a, and 280 may be comprised of macro-scale features, micro-scale features, and nano-scale features. For example, the roughened surface topography 80, 180, 180a, and 280 may be obtained by combining separate macro processing, micro processing, and nano processing steps. Macro features include relatively large dimensions, for example, dimensions measured in millimeters (mm) or microns (μm). Micro features include dimensions that are measured in microns (μm). Nano features include dimensions that are measured in nanometers (nm).

The shapes of the frictional surface protrusions of the roughened surface topography 80, 180, 180a, and 280 may be formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features when overlapping increase the surface contact area but do not result in undercuts that generate a cutting or aggressively abrasive action on the contacting bone surfaces.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The features may be divided into three size scales: nano, micro, and macro. The overlapping of the three feature sizes can be achieved using manufacturing processes that are completed sequentially and, therefore, do not remove or degrade the previous method.

The first step in the process may be mechanical (e.g., machining though conventional processes) or chemical bulk removal, for example, to generate macro features. The macro features may be of any suitable shape, for example, roughly spherical in shape, without undercuts or protruding sharp edges. Other shapes are possible, such as ovals, polygons (including rectangles), and the like. These features may be at least partially overlapped with the next scale (micro) of features using either chemical or mechanical methods (e.g., $AlO_2$ blasting) in predetermined patterns which also do not result in undercuts or protruding sharp edges. The third and final process step is completed through more mild (less aggressive) etching (e.g., HCl acid etching) that, when completed, generates surface features in both the micro and nano scales over both of the features generated by the two previous steps. The nano layer dictates the final chemistry of the implant material.

The macro features of the roughened surface topography 80, 180, 180a, and 280 are relatively large features. The macro features may be formed from subtractive techniques (e.g., mechanical or chemical bulk removal, for example) or additive techniques (e.g., deposition). Preferably, the macro features are formed by subtractive techniques, which remove portions of the surface (e.g., from the base material that was used to form the implant 1, 101, 101a, and 201). Suitable subtractive techniques may include, for example, machining (e.g., machine tools, such as saws, lathes, milling machines, and drill presses, are used with a sharp cutting tool to physically remove material to achieve a desired geometry) or masked etching (e.g., portions of the surface are protected by a masking material which resists etching and an etching substance is applied to unmasked portions). The patterns may be organized in regular repeating patterns and optionally overlap each other. In a preferred embodiment, the macro features may be formed in three, sequential steps.

The macro features may be produced by a heavy masked etching process, for example. Before etching, the surface may be cleaned and optionally blasted with an abrasive (e.g., alumina) in the areas to be chemically textured. Certain areas may be masked in a pattern using an etch resist and cured. The surface may then be chemically milled, for example, using a composition comprising hydrofluoric acid. The maskant and chemical milling may be repeated any number of times necessary to produce the desired pattern and etching depth. After the final etching process, the maskant may be removed and the part may be cleaned. The surface may also be passivated, for example, using an aqueous solution comprising nitric acid. The part may be cleaned and rinsed with water.

The macro features may be formed, for example, using three cut patterns. Specifically, a first cut pattern of the macro features may be formed in a surface (e.g., the top surface 10, 110, 110a, and 210). The "cut 1" features of the first cut pattern may cover about 20% of the total area of the surface, for example, leaving about 80% of the original surface remaining. The range of these percentages may be about ±20%, preferably ±10%, and more preferably about ±5%. The "cut 1" features of the first cut pattern do not have any undercuts. In one embodiment, these "cut 1" features have the smallest diameter and greatest depth of the macro features that are formed during the sequential steps.

A second cut pattern of the macro features may be formed in the surface. Together, the "cut 1" features of the first cut pattern and the "cut 2" features of the second cut pattern may cover about 85% of the total area of the surface, for example, leaving about 15% of the original surface remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of forming the macro features of the roughened surface topography 80, 180, 180a, and 280.

A third cut pattern of the macro features may be formed in the surface. Together, the "cut 1" features of the first cut pattern, the "cut 2" features of the second cut pattern, and the "cut 3" features of the third cut pattern may cover about 95% of the total area of the surface, for example, leaving about 5% of the original surface remaining. The range of these percentages may be about ±1%. In an embodiment of the invention, these "cut 3" features may have the largest diameter and least depth of the macro features that are formed during the sequential process steps.

The macro features are formed, additional process steps may be sequentially applied, in turn, to form the micro surface features (e.g., on the order of micrometers) of the roughened surface topography 80, 180, 180a, and 280. The micro features may also be formed from subtractive techniques (e.g., mechanical or chemical bulk removal, for example) or additive techniques (e.g., deposition). Preferably, the micro features are also formed by subtractive techniques.

In an exemplary embodiment, the micro features are removed by masked or unmasked etching, such as acid etching. For example, portions of the surface, including portions of the surface exposed by the macro step(s) described above, may be exposed to abrasive blasting, chemical etching, or both. The etching process may be repeated a number of times as necessitated by the amount and nature of the irregularities required for any particular application. Control of the strength of the etchant material, the temperature at which the etching process takes place, and the time allotted for the etching process allows fine control over the resulting surface produced by the process. The number of repetitions of the etching process can also be used to control the surface features.

By way of example, an etchant mixture of at least one of nitric acid and hydrofluoric acid may be repeatedly applied to a titanium surface to produce an average etch depth of about 0.53 mm. In another example, chemical modification of titanium can be achieved using at least one of hydrofluoric acid, hydrochloric acid, and sulfuric acid. In a dual acid etching process, for example, the first exposure is to hydrofluoric acid and the second is to a hydrochloric acid and sulfuric acid mixture. Chemical acid etching alone may enhance osteointegration without adding particulate matter (e.g., hydroxyapatite) or embedding surface contaminants (e.g., grit particles).

In one embodiment, the micro features are created by abrasive or grit blasting, for example, by applying a stream of abrasive material (such as alumina, sand) to the surface. In an exemplary embodiment, the micro features are created, at least partially, with an aqueous hydrochloric acid etching step and at least partially with an $AlO_2$ blasting step. Patterns may be organized in regular repeating patterns and optionally overlap each other. After the micro features are formed, it is possible that less than about 3% of the original surface remains. The range of that percentage may be about ±1%.

After the macro features and micro features are formed, additional process steps may be sequentially applied, in turn, to form the nano surface features of the roughened surface topography 80, 180, 180a, and 280. The nano features may also be formed from subtractive techniques (e.g., mechanical or chemical bulk removal, for example) or additive techniques (e.g., deposition). Preferably, the nano features are also formed by subtractive techniques.

In an exemplary embodiment, the nano features are removed by masked or unmasked etching. For example, portions of the surface, including portions of the surface exposed by the macro and micro steps described above, may be exposed to a chemical etching. In an exemplary embodiment, the nano process also includes an acid etching, with a strong or weak acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The acid etching process for the nano step is preferably less aggressive than the acid etching process in the macro or micro steps. In other words, a less acidic, mild, or more diluted acid may be selected. In an exemplary embodiment, the nano features are created, at least partially, with an aqueous hydrochloric acid etching step.

As an example, the nano features (or micro features) may be formed by preparing an acid solution comprising hydrochloric acid, water, and titanium; applying the acid solution to the surface; removing the acid solution by rinsing with water; and heating and subsequently cooling the surface.

The acid solution may be prepared using any suitable techniques known in the art. For example, the acid solution may be prepared by combining hydrochloric acid and water, simultaneously or sequentially. The aqueous hydrochloric acid solution may optionally be heated, for example, to a temperature of about 150-250° F. (66-121° C.), preferably about 200-210° F. (93-99° C.), and most preferably about 205° F. (96° C.). The titanium may be seeded (e.g., added) in the aqueous hydrochloric acid solution or may already be present from titanium previously removed from at least one surface of the implant 1, 101, 101a, and 201, for example, in a continuous manufacturing process. The solution may optionally be cooled. The acid solution may comprise a concentration of 20-40% hydrochloric acid, preferably about 25-31% hydrochloric acid, and more preferably about 28% hydrochloric acid, based on the weight percent of the solution.

The acid solution may be applied to the surface using any suitable mechanism or techniques known in the art, for example, immersion, spraying, brushing, and the like. In an exemplary embodiment, the acid solution is applied by immersing the entire part in the solution. It is also contemplated that the surface may be immersed in the acid solution alone or in combination with the assembled implant 1, 101, 101a, and 201. If desired, certain areas of the surface or the implant 1, 101, 101a, and 201 may be masked in patterns or to protect certain portions of the implant 1, 101, 101a, and 201. The acid solution may be heated when it is applied. For example, the solution may be heated to a temperature of about 150-250° F. (66-121° C.), preferably about 200-210° F. (93-99° C.), and most preferably about 205° F. (96° C.). The solution may also be applied for any suitable period of time. For example, the solution may be applied for a period of time of about 5-30 minutes, preferably about 15-25 minutes, and more preferably about 20 minutes.

After the acid solution is applied, the acid solution may be removed, for example, by rinsing with water (e.g., deionized water). The surface or entire implant 1, 101, 101a, and 201, may be subsequently dried. The surface may be dried using any suitable mechanism or techniques known in the art, for example, by heating in an oven (e.g., a dry oven). The surface may be heated to a temperature of about 110-130° F. (43-54° C.), preferably about 120-125° F. (49-52° C.), and most preferably about 122.5° F. (50° C.). The surface may be heated for any suitable period of time, for example about 30-50 minutes, preferably about 35-45 minutes, and more preferably about 40 minutes. After heating, the surface may be cooled to room temperature, for example.

It is contemplated that the nano features may also be created by the abrasive or grit blasting, for example, described for the micro processing step. Patterns may be organized in regular repeating patterns and optionally overlap each other. The nano features may also be achieved by tumble finishing (e.g., tumbling) the part or the implant 1, 101, 101a, and 201. Suitable equipment and techniques can be selected by one of ordinary skill in the art. For example, a barrel may be filled with the parts or implants 1, 101, 101a, and 201 and the barrel is then rotated. The parts or implants 1, 101, 101a, and 201 may be tumbled against themselves or with steel balls, shot, rounded-end pins, or ballcones. The tumbling process may be wet (e.g., with a lubricant) or dry. After the nano features are formed, it is possible that less than about 1% of the original surface remains. For example, after the nano features are formed, the roughened surface topography 80, 180, 180a, and 280 may cover substantially all of the top surface 10, 110, 110a, and 210 and/or bottom surface 20, 120, 120a, and 220 of the implant 1, 101, 101a, and 201 in contact with the vertebral endplate (except for the rounded edges.

Any or each of the steps, including the macro, micro, or nano processing steps, may be accompanied by a cleaning step. In addition, the part may be cleaned once the processing steps are complete. For example, the part may be washed in an aqueous environment under agitation and heat with or without a detergent. Following washing, the part may be dried, for example with hot air, heating in a dry oven, or both.

The process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the roughened surface topography 80, 180, 180a, and 280 of the implant 1, 101, 101a, and 201 should be oriented in opposition to the biologic forces on the implant 1, 101, 101a, and 201 and to the insertion direction. In one particular embodiment, for example, the pattern of the roughened surface topography 80, 180, 180a, and 280 may be modeled after an S-shaped tire tread.

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Surface roughness may be measured using a laser profilometer or other standard instrumentation.

Figure 30:
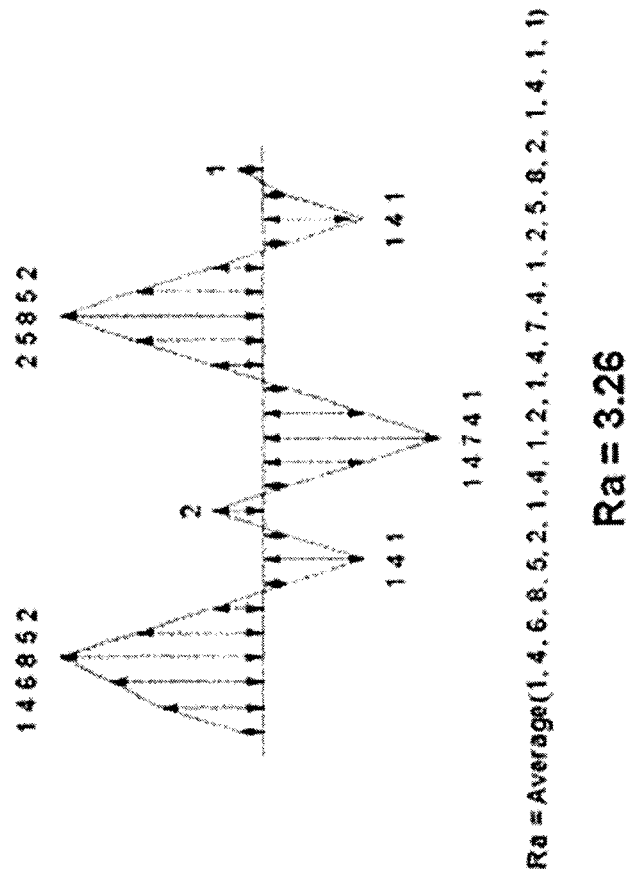
FIG. 30 shows a graphic representation of the average amplitude, Ra.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peakto-valley height, Rmax; (4) total peak-to-valley of waviness profile, Wt; and (5) mean spacing, Sm. In practice, "Ra" is the most commonly used roughness parameter. It is the arithmetic average height. Mathematically, Ra is computed as the average distance between each roughness profile point and the mean line. In FIG. 30, the average amplitude is the average length of the arrows.

In mathematical terms, this process can be represented as Equation 1:

$$Ra = \frac{1}{n}\sum_{i=1}^{n} |y_i|$$

Figure 31:
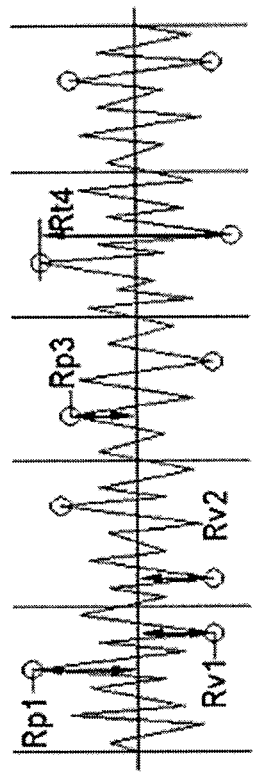
FIG. 31 shows a graphic representation of the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 31.

Figure 32:
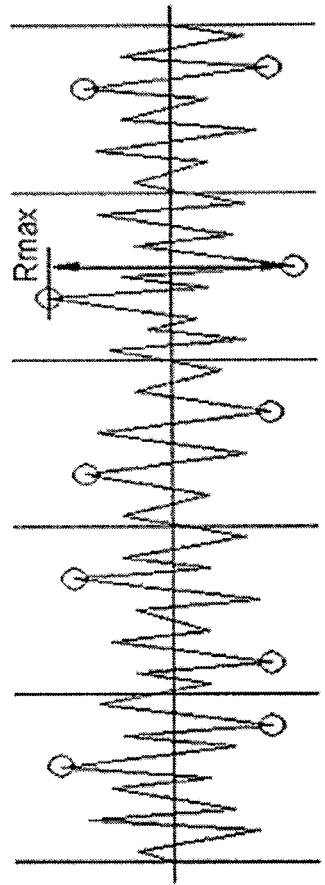
FIG. 32 shows a graphic representation of the maximum peak-to-valley height, Rmax.
Figure 33:
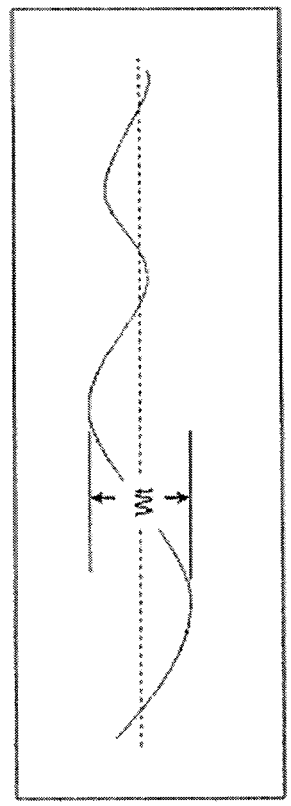
FIG. 33 shows a graphic representation of the total peak-to-valley waviness profile
Figure 34:
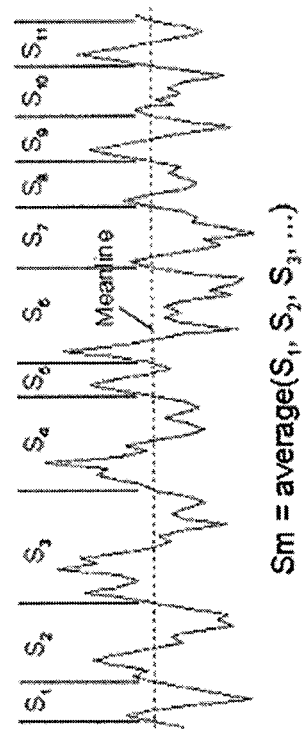
FIG. 34 shows a graphic representation of the mean spacing, Sm.
Figure 35:
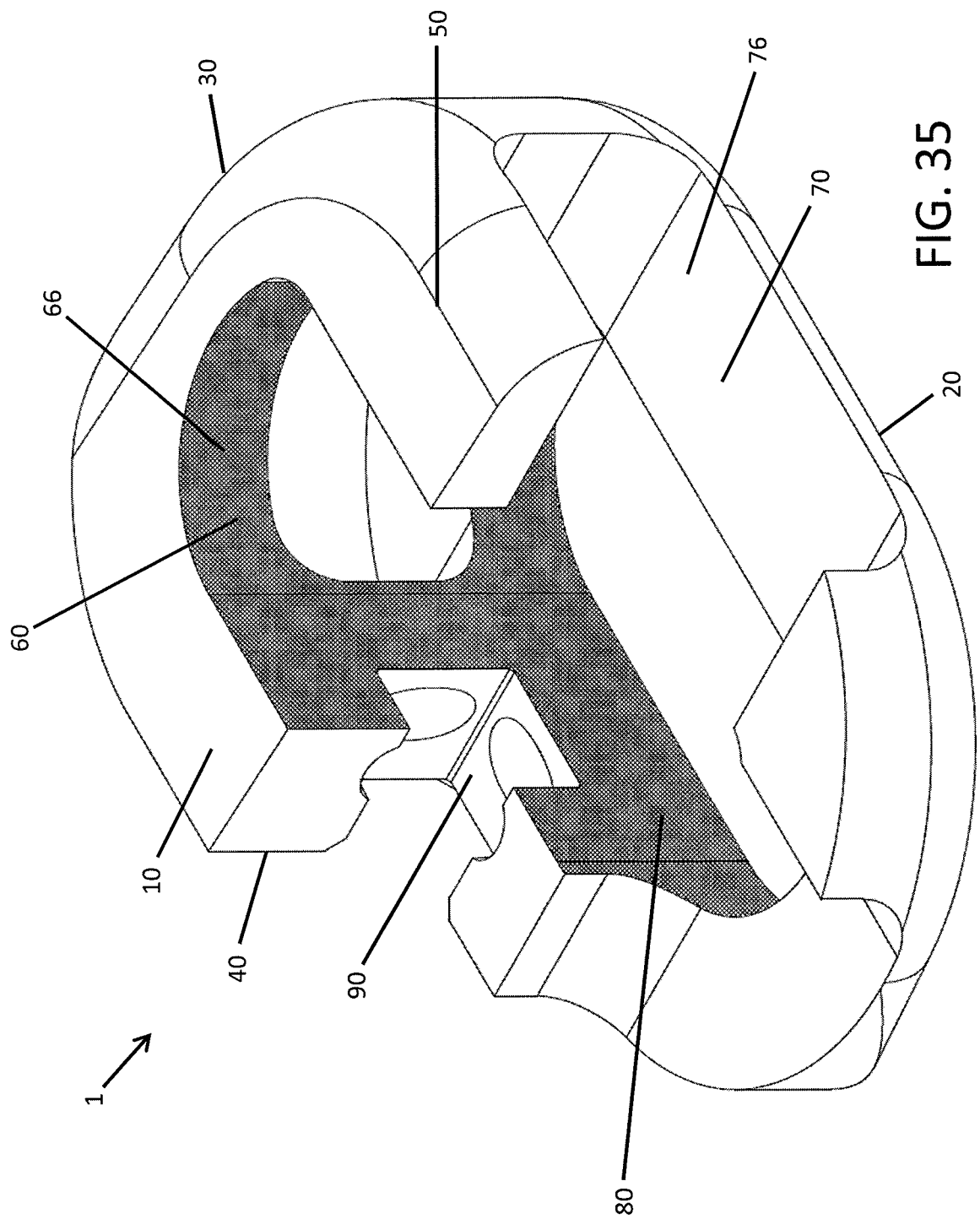
FIG. 35 shows a cut-away view of an anterior lumbar interbody fusion implant having roughened surface topography on the internal surfaces of the vertical aperture and hollow center.
Figure 36:
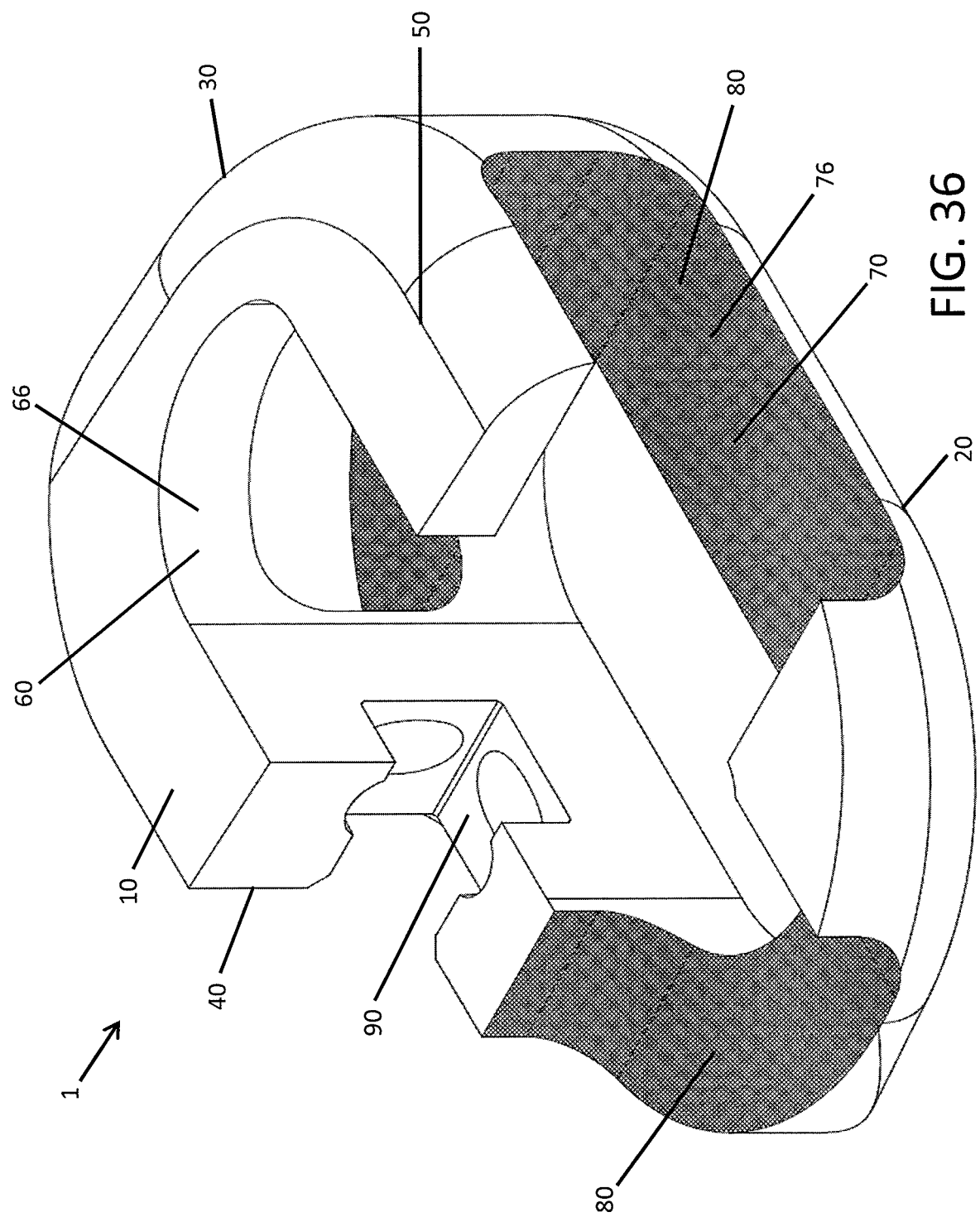
FIG. 36 shows a shows a cut-away view of an anterior lumbar interbody fusion implant having roughened surface topography on the internal surfaces of the transverse aperture.
Figure 37:
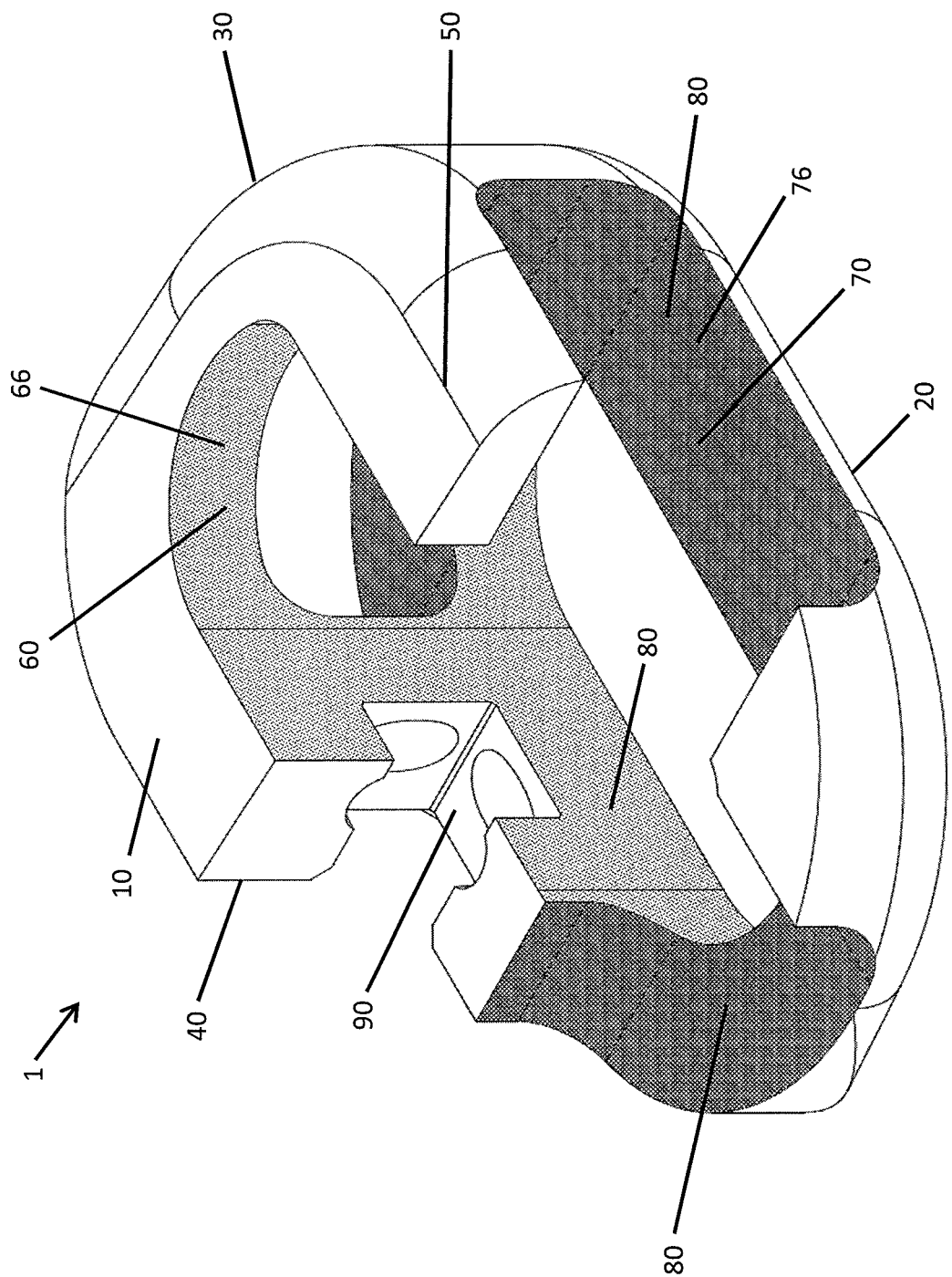
FIG. 37 shows a cut-away view of an anterior lumbar interbody fusion implant having roughened surface topography on the internal surfaces of the vertical aperture and hollow center, and transverse aperture.
Figure 38:
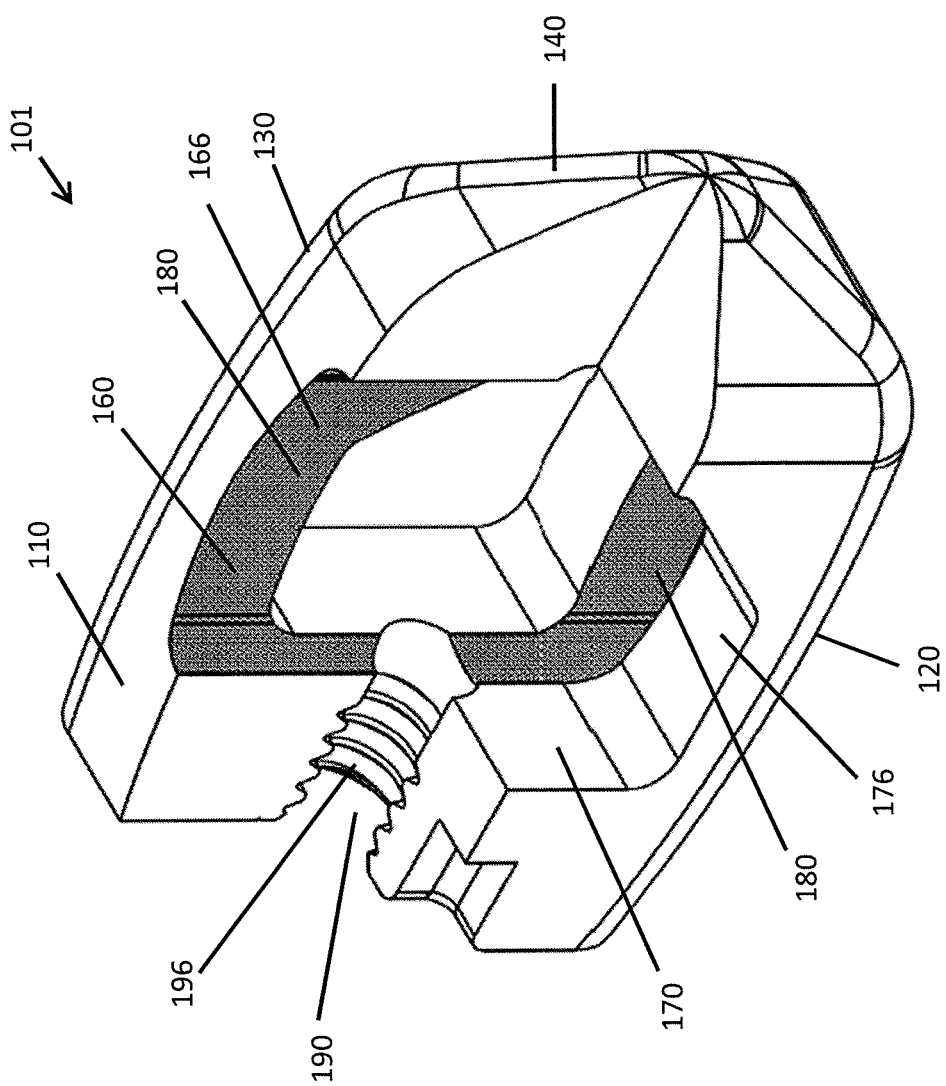
FIG. 38 shows a cut-away view of a posterior lumbar interbody fusion implant having roughened surface topography on the internal surfaces of the vertical aperture and hollow center.
Figure 39:
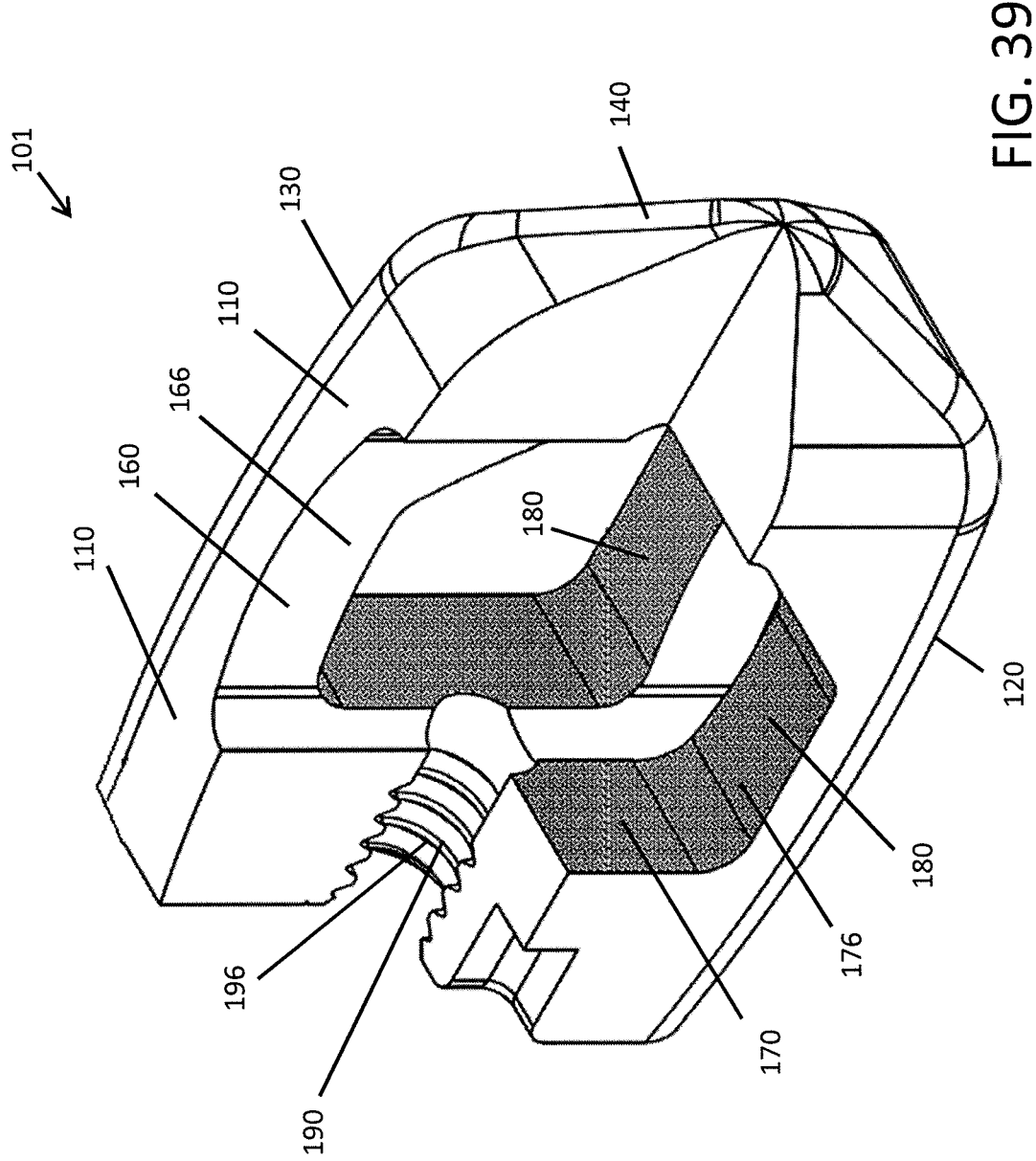
FIG. 39 shows a cut-away view of a posterior lumbar interbody fusion implant having roughened surface topography on the internal surfaces of the transverse aperture.
Figure 40:
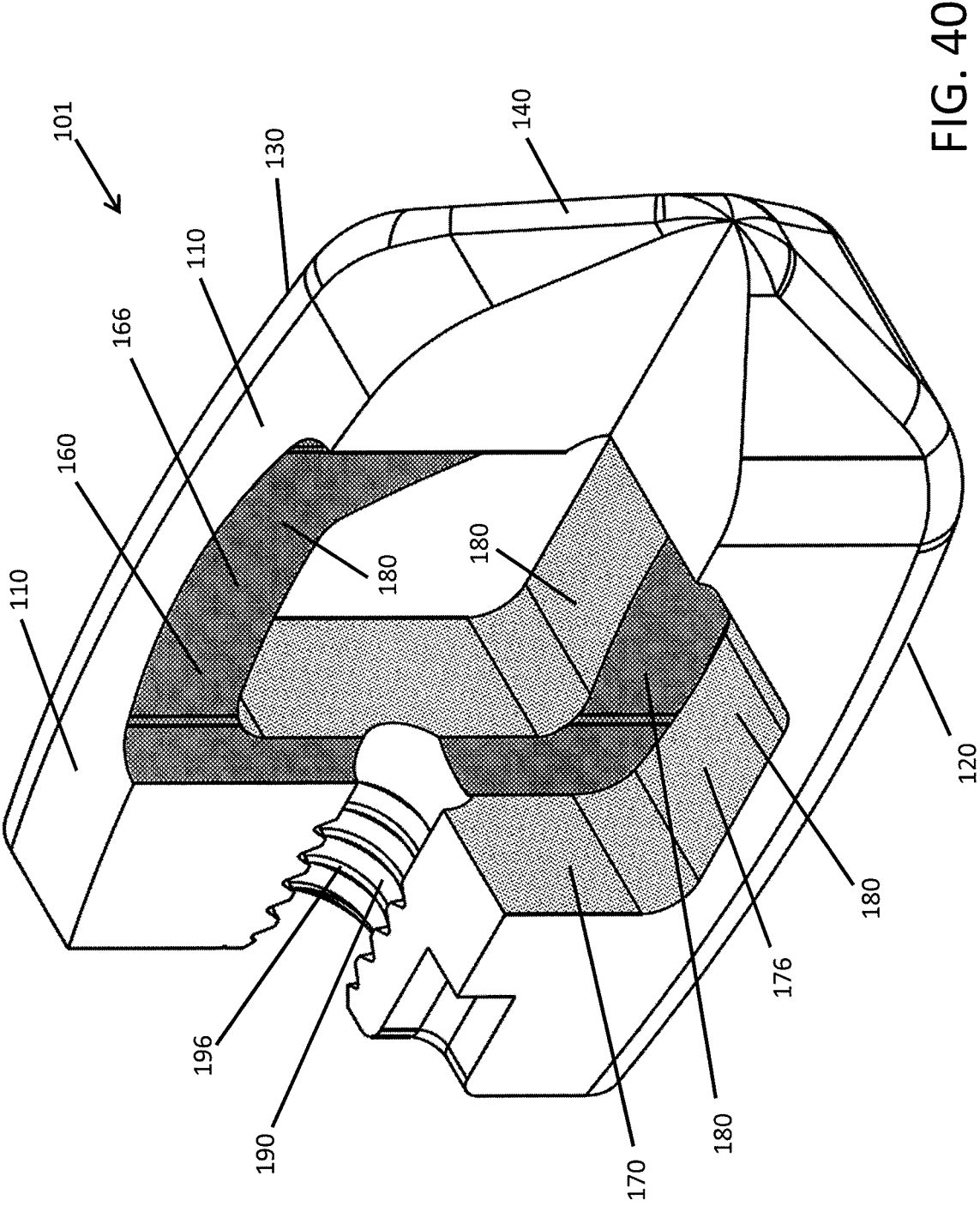
FIG. 40 shows a cut-away view of a posterior lumbar interbody fusion implant having roughened surface topography on the internal surfaces of the vertical aperture and hollow center, and transverse aperture.
Figure 41:
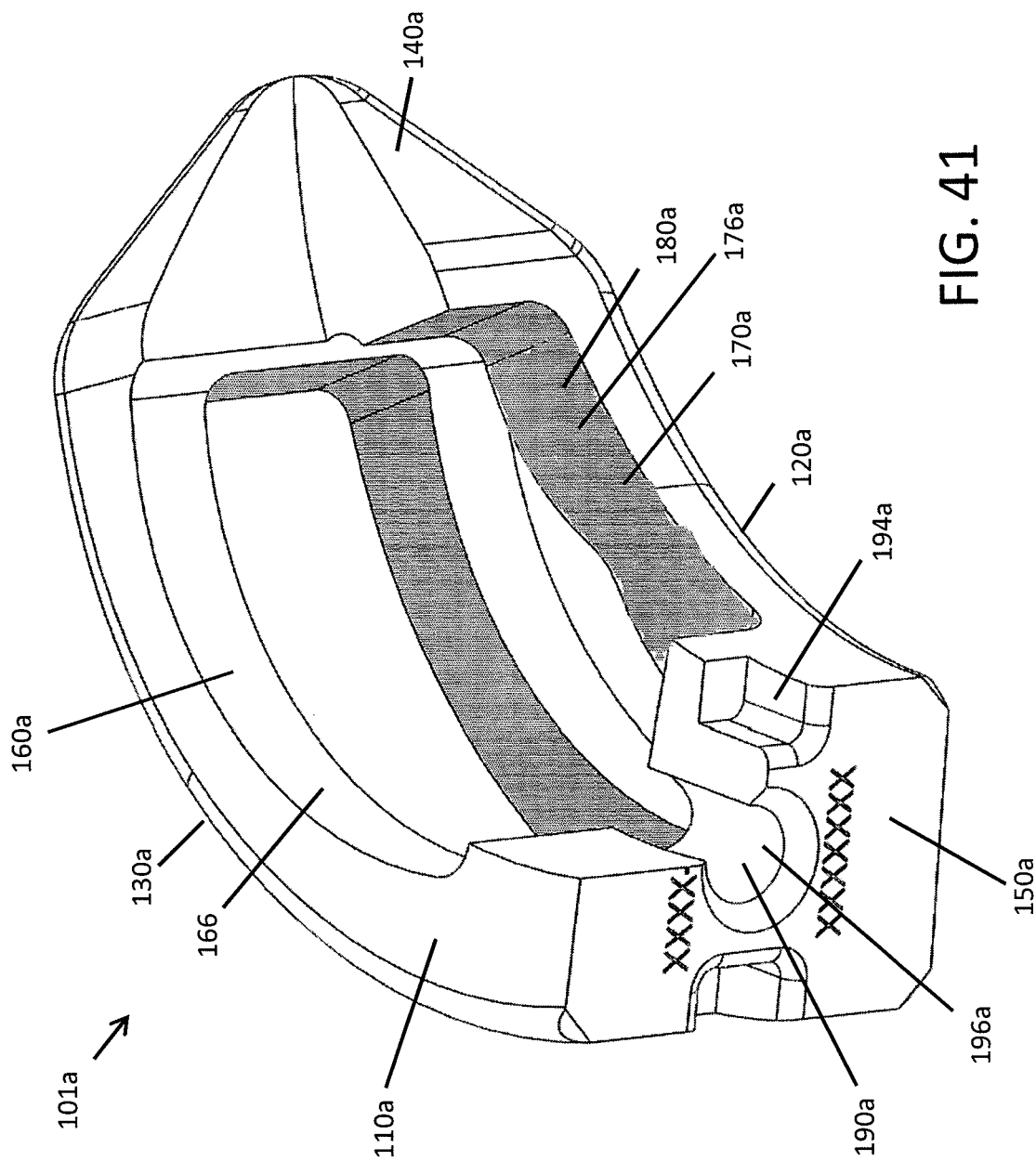
FIG. 41 shows a shows a cut-away view of a curved posterior lumbar interbody fusion implant having roughened surface topography on the internal surfaces of the transverse aperture.
Figure 42:
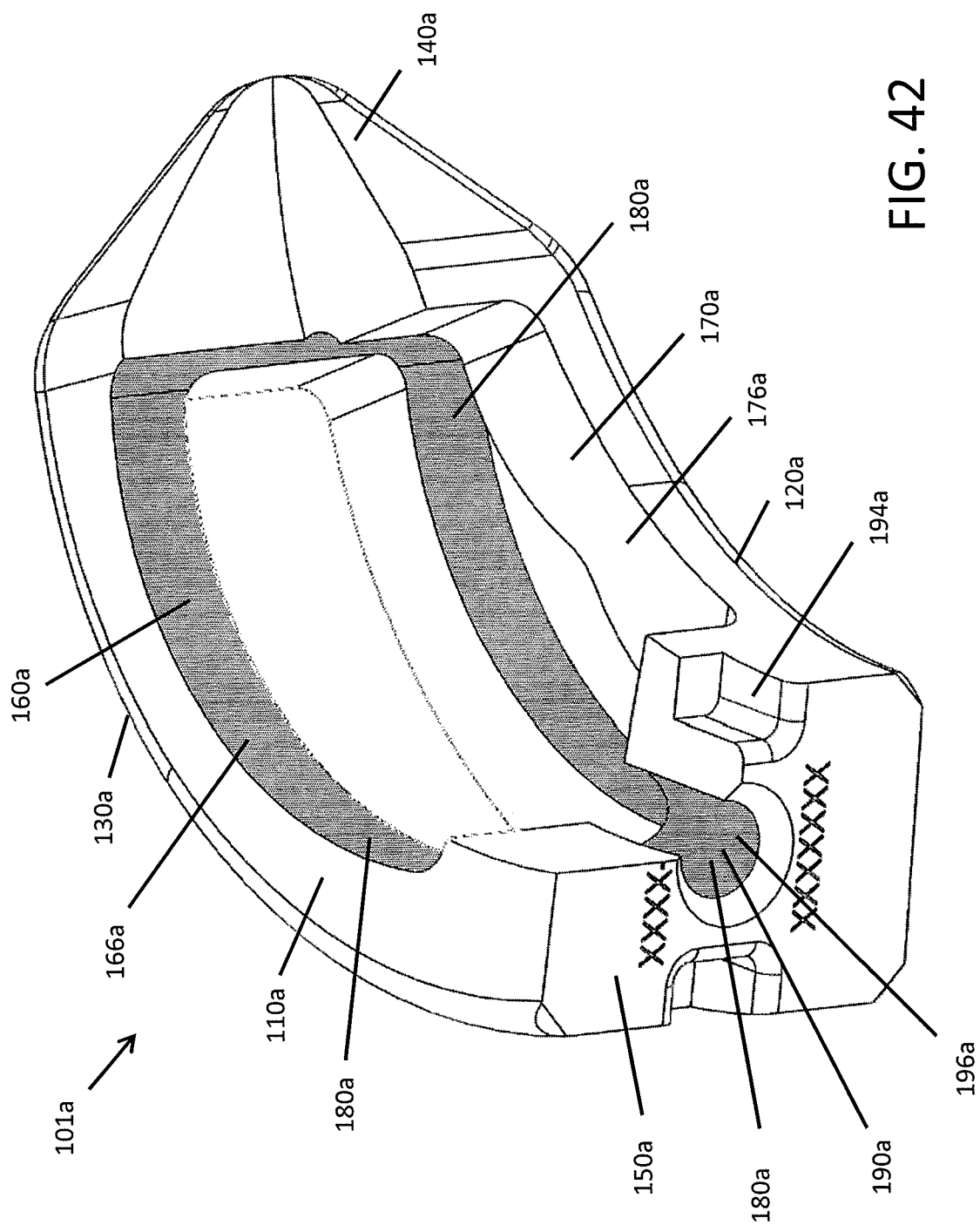
FIG. 42 shows a cut-away view of a curved posterior lumbar interbody fusion implant having roughened surface topography on the internal surfaces of the vertical aperture and hollow center.
Figure 43:
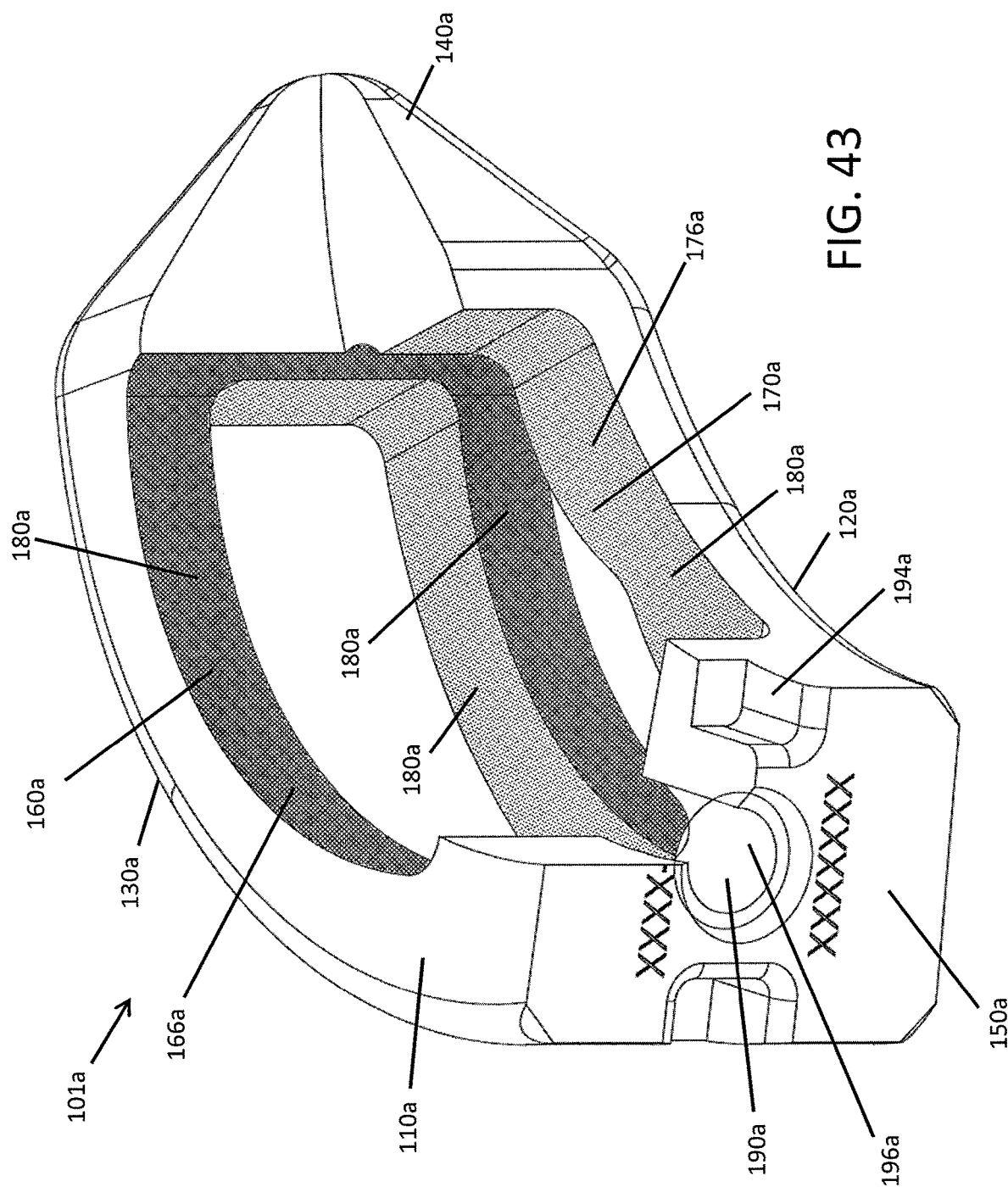
FIG. 43 shows a cut-away view of a curved posterior lumbar interbody fusion implant having roughened surface topography on the internal surfaces of the vertical aperture and hollow center, and transverse aperture.

The maximum peak-to-valley height, Rmax, is the maximum peak-to-valley distance in a single sampling length as illustrated in FIG. 32. The total peak-to-valley of waviness profile (over the entire assessment length) is illustrated in FIG. 33. The mean spacing, Sm, is the average spacing between positive mean line crossings. The distance between each positive (upward) mean line crossing is determined and the average value is calculated, as illustrated in FIG. 34.

The parameters Sm, Rmax, and Ra can be used define the surface roughness following formation of each of the three types of features macro, micro, and nano. Such data are provided in Tables 1-3.

TABLE 1

Surface Feature Size and Roughness (Metric): Macro (μm)

|  | Size (Sm) | Depth (Rmax) | Roughness (Ra) |
| --- | --- | --- | --- |
| Max. | 2,000 | 500 | 200 |
| Min. | 400 | 40 | 20 |
| Avg. | 1,200 | 270 | 110 |

TABLE 2

Surface Feature Size and Roughness (Metric): Micro (μm)

|  | Size (Sm) | Depth (Rmax) | Roughness (Ra) |
| --- | --- | --- | --- |
| Max. | 400 | 40 | 20 |
| Min. | 20 | 2 | 1 |
| Avg. | 210 | 11 | 5.5 |

TABLE 3

Surface Feature Size and Roughness (Metric): Nano (μm)

|  | Size (Sm) | Depth (Rmax) | Roughness (Ra) |
| --- | --- | --- | --- |
| Max. | 20 | 2 | 1 |
| Min. | 0.5 | 0.2 | 0.01 |
| Avg. | 10.25 | 1.1 | 0.505 |

Based on the data in Table 1, the macro features for each of the three parameters may comprise the following preferred ranges (all measurements in microns). In some aspects, the macro mean spacing, Sm, is about 400 to about 2000 micrometers. More preferably, the macro mean spacing is about 750 to about 1750 micrometers, and more preferably, the macro mean spacing is about 1000 to about 1500 micrometers. In some aspects, the macro mean spacing is about 500 to about 1000 micrometers, about 600 to about 900 micrometers, about 700 to about 1000 micrometers, about 750 to about 1200 micrometers, about 800 to about 1300 micrometers, about 900 to about 1300 micrometers, about 1000 to about 1300 micrometers, about 1100 to about 1300 micrometers, about 1100 to about 1400 micrometers, about 1150 to about 1250 micrometers, about 1150 to about 1350 micrometers, about 1200 to about 1500 micrometers, or about 1200 to about 1400 micrometers. In some aspects, the macro peak-to-valley height, Rmax, is about 40 to about 500 micrometers. More preferably, the macro peak-to-valley height is about 150 to about 400 micrometers, and more preferably, about 250 to about 300 micrometers. In some aspects, the macro mean peak-to valley height is about 100 to about 450 micrometers, about 200 to about 400 micrometers, about 200 to about 300 micrometers, about 260 to about 280 micrometers, about 250 to about 350 micrometers, about 260 to about 320 micrometers, or about 270 to about 300 micrometers. In some aspects, the macro average amplitude, Ra, is about 20 to about 200 micrometers. More preferably, the macro average amplitude is about 50 to about 150 micrometers, and more preferably about 100 to about 120 micrometers. In some aspects, the macro average amplitude is about 80 to about 180 micrometers, about 90 to about 160 micrometers, about 90 to about 140 micrometers, about 100 to about 150 micrometers, about 100 to about 130 micrometers, about 105 to about 125 micrometers, or about 105 to about 115 micrometers.

Based on the data in Table 2, the micro features for each of the three parameters may comprise the following preferred ranges (all measurements in microns). In some aspects, the micro mean spacing, Sm, is about 20 to about 400 micrometers. More preferably, the micro mean spacing is about 100 to about 300 micrometers, and more preferably, the macro mean spacing is about 200 to about 220 micrometers. In some aspects, the micro mean spacing is about 50 to about 350 micrometers, about 75 to about 350 micrometers, about 75 to about 300 micrometers, about 100 to about 325 micrometers, about 100 to about 250 micrometers, about 120 to about 220 micrometers, about 150 to about 250 micrometers, about 180 to about 240 micrometers, about 190 to about 230 micrometers, or about 205 to about 215 micrometers. In some aspects, the micro peak-to-valley height, Rmax, is about 2 to about 40 micrometers. More preferably, the micro peak-to-valley height is about 5 to about 25 micrometers, and more preferably, about 6 to about 16 micrometers. In some aspects, the micro mean peak-to valley height is about 0.5 to about 50 micrometers, about 1 to about 45 micrometers, about 1 to about 40 micrometers, about 1 to about 30 micrometers, about 1 to about 20 micrometers, about 1 to about 15 micrometers, about 2 to about 50 micrometers, about 2 to about 30 micrometers, about 2 to about 25 micrometers, about 3 to about 40 micrometers, about 3 to about 30 micrometers, about 4 to about 40 micrometers, about 4 to about 30 micrometers, about 5 to about 40 micrometers, about 5 to about 30 micrometers, about 7 to about 20 micrometers, about 7 to about 15 micrometers, about 8 to about 14 micrometers, or about 9 to about 13 micrometers. In some aspects, the micro average amplitude, Ra, is about 1 to about 20 micrometers. More preferably, the micro average amplitude is about 1 to about 10 micrometers, and more preferably about 3 to about 7 micrometers. In some aspects, the micro average amplitude is about 0.5 to about 30 micrometers, about 0.5 to about 25 micrometers, about 1 to about 15 micrometers, about 1 to about 10 micrometers, about 1 to about 9 micrometers, about 1 to about 7 micrometers, about 2 to about 9 micrometers, or about 4 to about 7 micrometers.

Based on the data in Table 3, the nano features for each of the three parameters may comprise the following preferred ranges (all measurements in microns). In some aspects, the nano mean spacing, Sm, is about 0.5 to about 20 micrometers. More preferably, the nano mean spacing is about 5 to about 15 micrometers, and more preferably, the macro mean spacing is about 8 to about 12 micrometers. In some aspects, the nano mean spacing is about 0.1 to about 30 micrometers, about 0.25 to about 25 micrometers, about 0.5 to about 15 micrometers, about 0.5 to about 13 micrometers, about 1 to about 250 micrometers, about 1 to about 20 micrometers, about 1 to about 150 micrometers, about 2 to about 18 micrometers, about 2 to about 12 micrometers, about 7 to about 14 micrometers, or about 9 to about 11.5 micrometers. In some aspects, the nano peak-to-valley height, Rmax, is about 0.2 to about 2 micrometers. More preferably, the nano peak-to-valley height is about 0.5 to about 1.5 micrometers, and more preferably, about 0.8 to about 1.4 micrometers. In some aspects, the nano mean peak-to-valley height is about 0.05 to about 5 micrometers, about 0.1 to about 3 micrometers, about 0.1 to about 2 micrometers, about 0.1 to about 1.5 micrometers, about 0.1 to about 0.4 micrometers, about 0.2 to about 3 micrometers, about 0.2 to about 2.5 micrometers, about 0.2 to about 1.8 micrometers, about 0.6 to about 1.6 micrometers, about 0.7 to about 1.5 micrometers, or about 0.9 to about 1.3 micrometers. In some aspects, the nano average amplitude, Ra, is about 0.01 to about 1 micrometers. More preferably, the nano average amplitude is about 0.05 to about 0.75 micrometers, and more preferably about 0.3 to about 0.7 micrometers. In some aspects, the nano average amplitude is about 0.005 to about 2 micrometers, about 0.005 to about 1.5 micrometers, about 0.01 to about 0.75 micrometers, about 0.01 to about 1.1 micrometers, about 0.01 to about 0.9 micrometers, about 0.01 to about 0.07 micrometers, about 0.025 to about 0.75 micrometers, or about 0.04 to about 0.6 micrometers.

Figure 44:
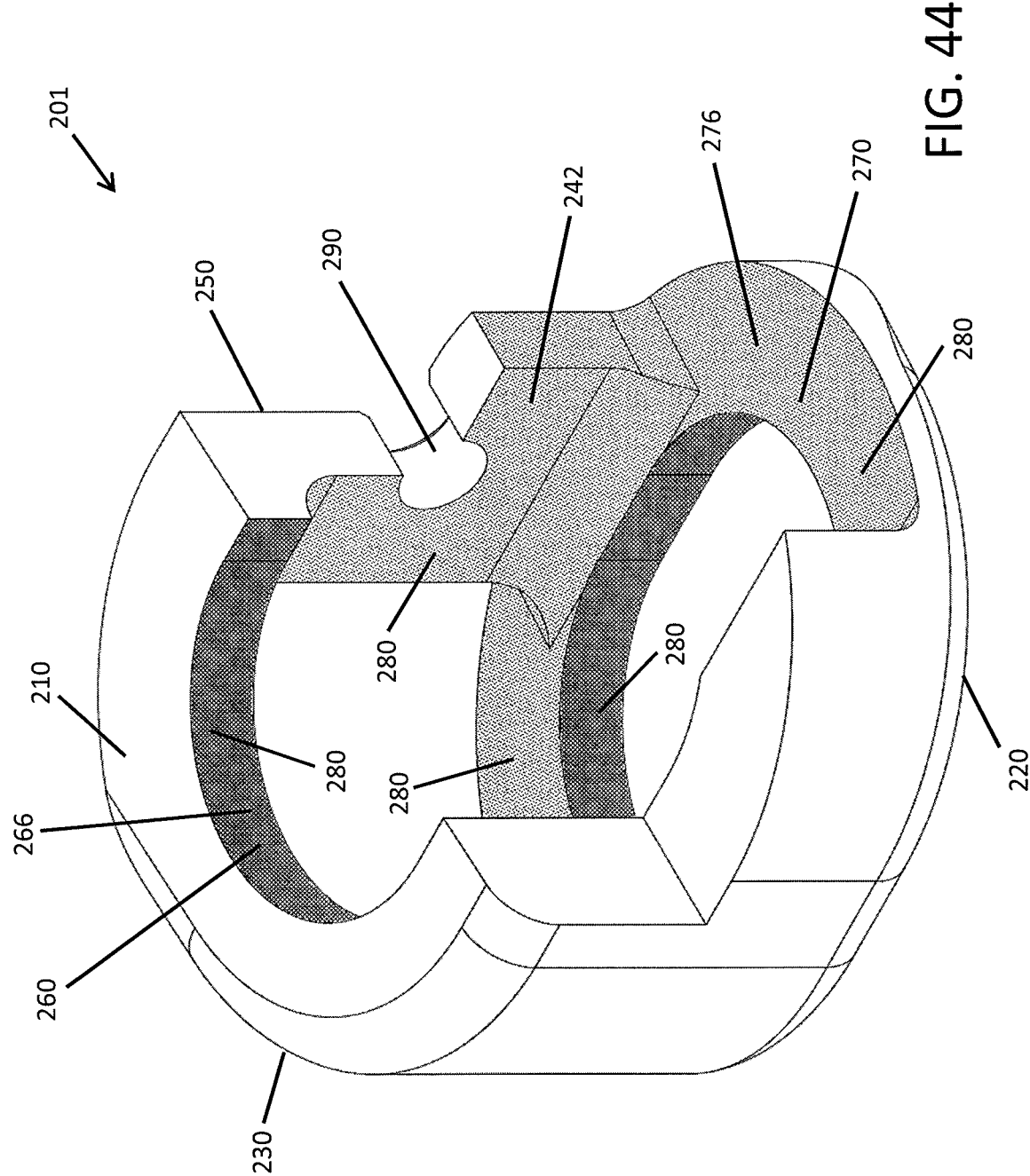
FIG. 44 shows a cut-away view of a cervical fusion implant having roughened surface topography on the internal surfaces of the vertical aperture and hollow center, transverse aperture, and rear wall; and, FIG. 45 shows a shows a cut-away view of a cervical fusion implant having roughened surface topography on the internal surfaces of the vertical aperture and the transverse aperture.
Figure 45:
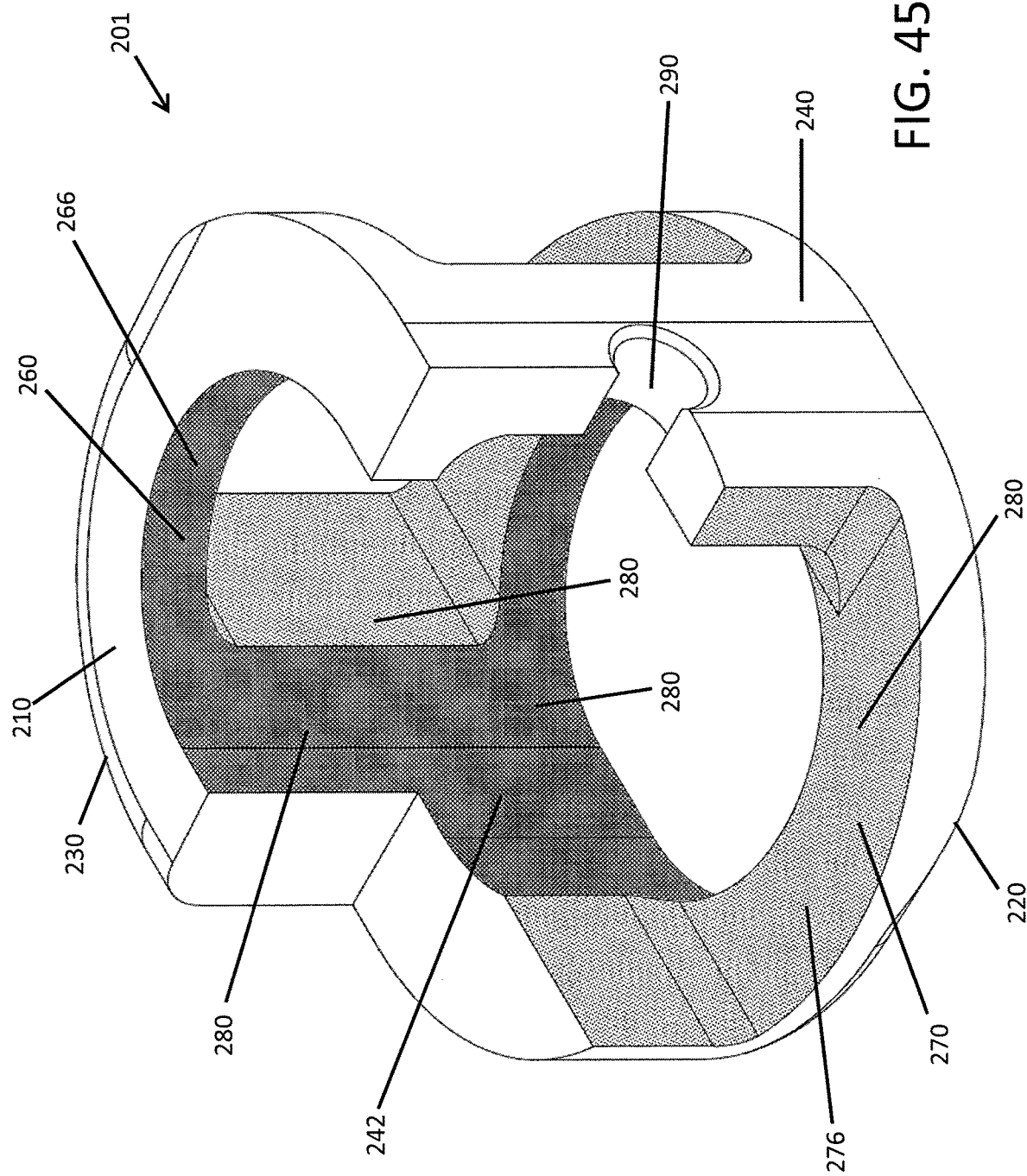

In addition to the top surface 10, 110, 110a, and 210, and bottom surface 20, 120, 120a, and 220, the roughened surface topography 80, 180, 180a, and 280 may also be present on at least a portion of one or more internal surfaces of the implant 1, 101, 101a, and 201, particularly those surfaces that will be in contact with a bone graft material. The internal surfaces having a roughened surface topography 80, 180, 180a, and 280 include the surfaces of the interior of the implant 1, 101, 101a, and 201 that surround and define the substantially hollow center, and include the sidewalls 66, 166, 166a, and 266 of the vertical aperture 60, 160, 160a, and 260 (see, e.g., FIGS. 35, 37, 38, 40, 42, and 43-45), the sidewalls 76, 176, 176a, and 276 of the transverse aperture 70, 170, 170a, and 270 (see, e.g., FIGS. 36, 37, 39, 40, 41, and 43-45), the internal surfaces of the intermediate wall 172, 172a, the surfaces of the sidewalls 96, 196, 196a, and 296 of the opening 90, 190, 190a, and 290, the surfaces of the implant holding feature 194, and 194a (not shown), and the internal surfaces of the rear wall 242 (FIGS. 44 and 45). The internal roughened surface topography 80, 180, 180a, and 280 may be present on any one or combination of these internal surfaces, and not all such internal surfaces need to have any roughened surface topography 80, 180, 180a, and 280 on any given implant 1, 101, 101a, and 201, although the implant 1, 101, 101a, and 201 nevertheless will have roughened surface topography on the top surface 10, 110, 110a, and 210 and/or bottom surface 20, 120, 120a, and 220 in addition to the internal surfaces that are roughened. The roughened surface topography 80, 180, 180a, and 280 on such internal surfaces may comprise the Sm, Rmax, and Sa features described above. The roughened surface topography 80, 180, 180a, and 280 on such internal surfaces preferably promotes osseointegration when the implant 1, 101, 101a, and 201 is implanted within the intervertebral space, for example, when a bone graft material is placed within the substantially hollow center, including within one or more of the vertical aperture 60, 160, 160a, and 260 and the transverse aperture 70, 170, 170a, and 270.

The following examples are provided to describe the invention in greater detail. They are intended to illustrate, not to limit, the invention.

Example 1

Figures 7, 8, 9:
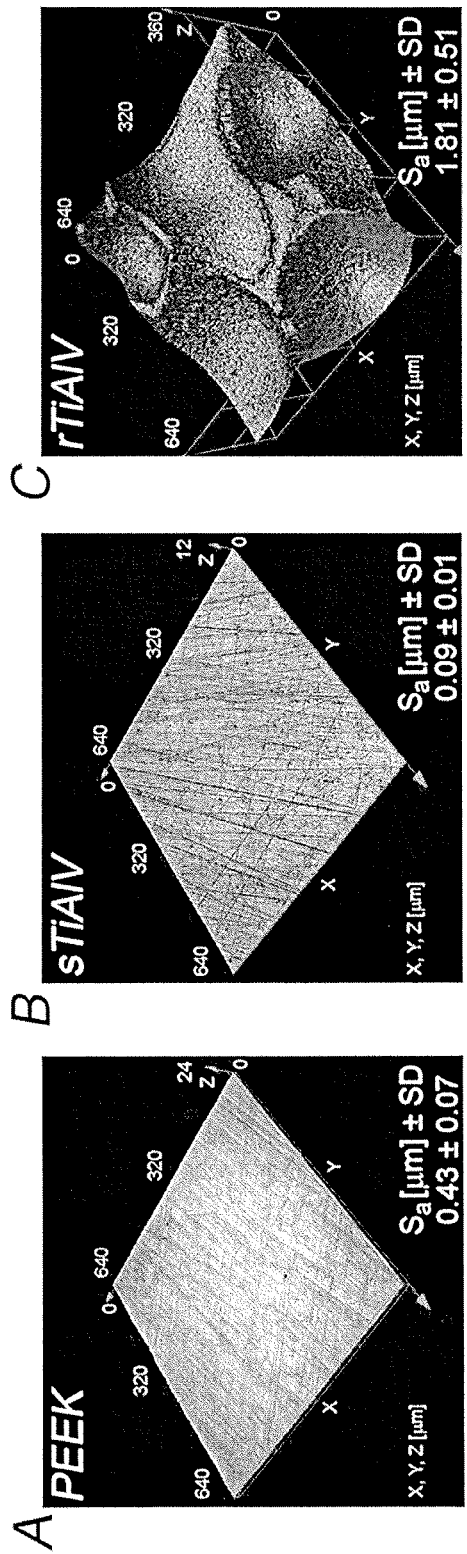
FIG. 7 shows a confocal laser microscopy image of an comparative polyetheretherketone (PEEK) surface.
FIG. 8 shows a confocal laser microscopy image of a comparative smooth titanium alloy (sTi or sTiAlV) surface.
FIG. 9 shows a confocal laser microscopy image of an exemplary rough titanium alloy (rTi or rTiAlV) surface.
Figures 10, 11, 12:
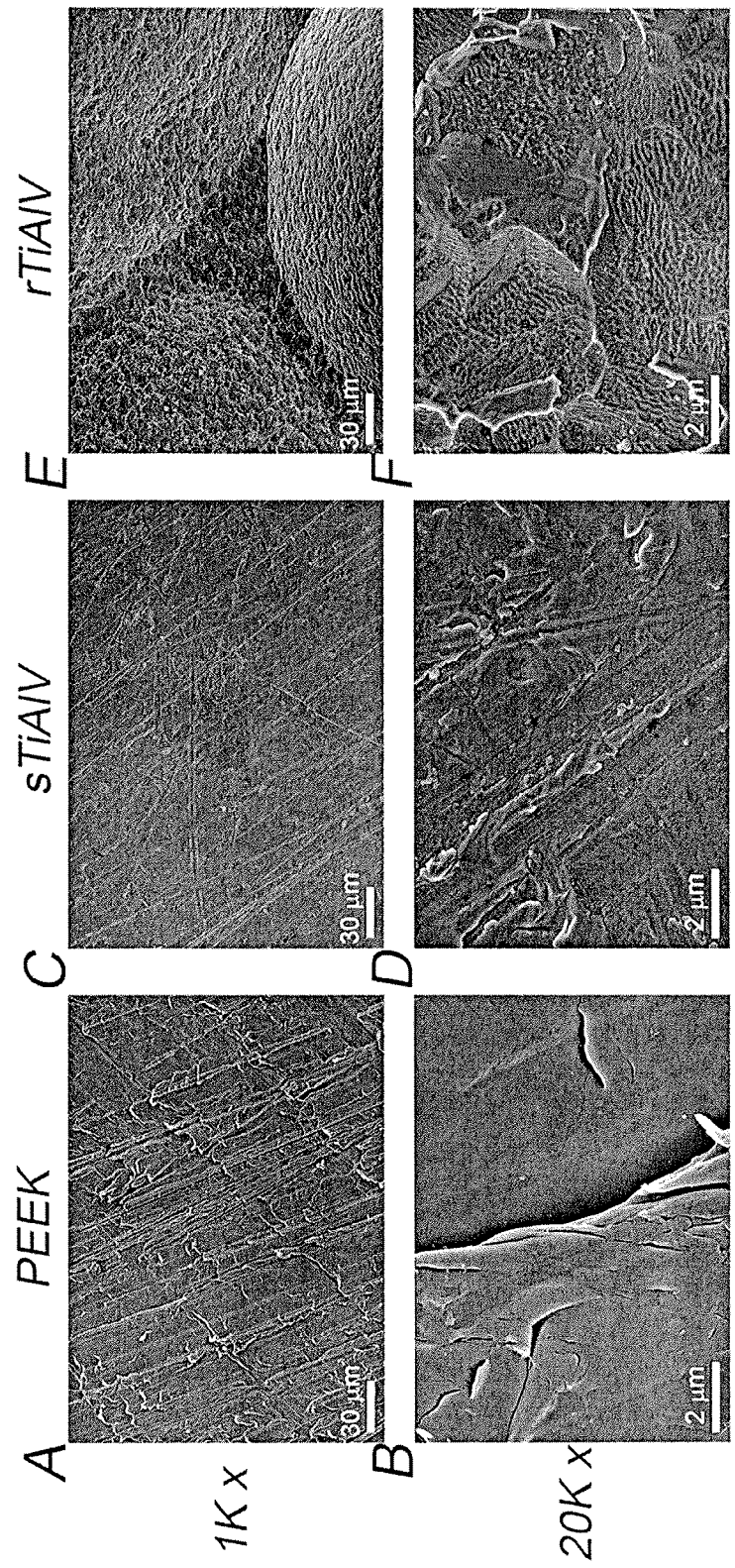
FIG. 10 shows SEM images of the PEEK surface of FIG. 7 at 1K× and 2K× magnification.
FIG. 11 shows SEM images of the smooth titanium alloy surface of FIG. 8 at 1K× and 2K× magnification.
FIG. 12 shows SEM images of the rough titanium alloy surface of FIG. 9 at 1K× and 2K× magnification.
Figure 13:
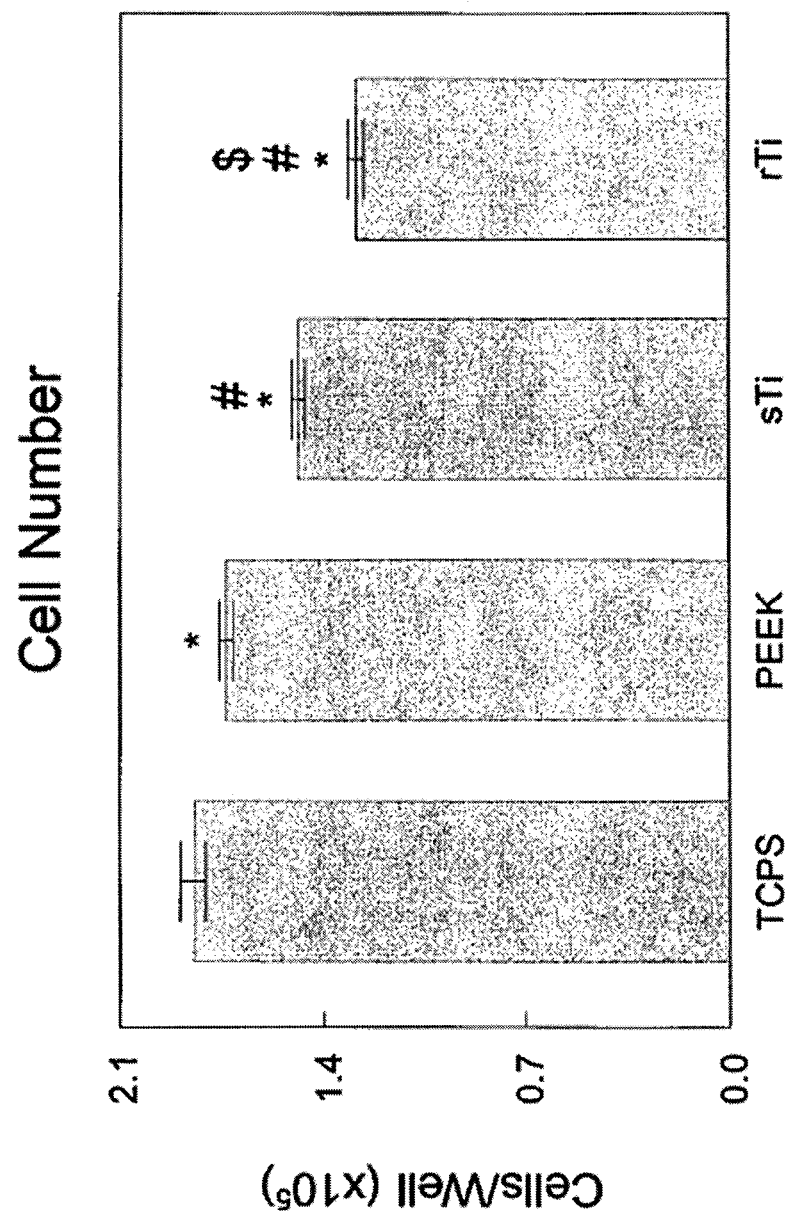
FIG. 13 shows a graph of the cell number for human MG63 osteoblast-like cells cultured on tissue culture polystyrene (TCPS), PEEK, sTI, and rTi surfaces.
Figure 14:
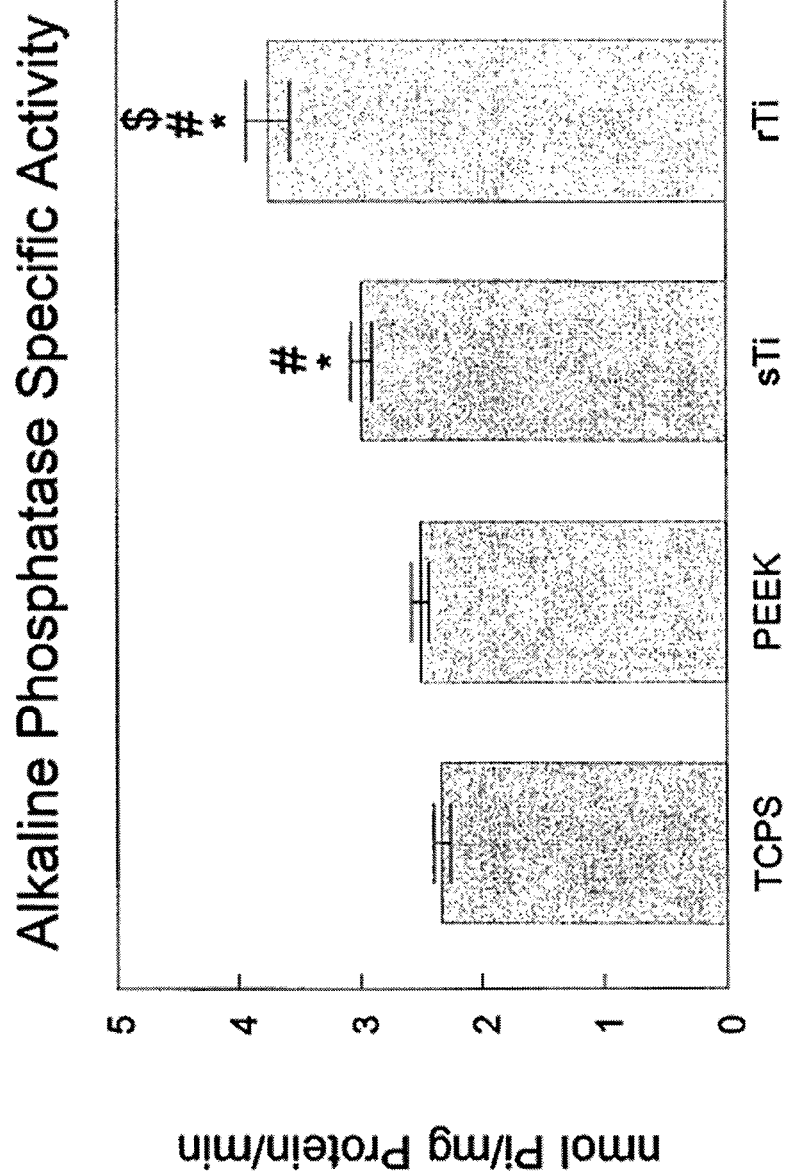
FIG. 14 shows a graph of alkaline phosphatase specific activity for human MG63 osteoblast-like cells cultured on tissue culture polystyrene (TCPS), PEEK, sTI, and rTi surfaces.
Figure 15:
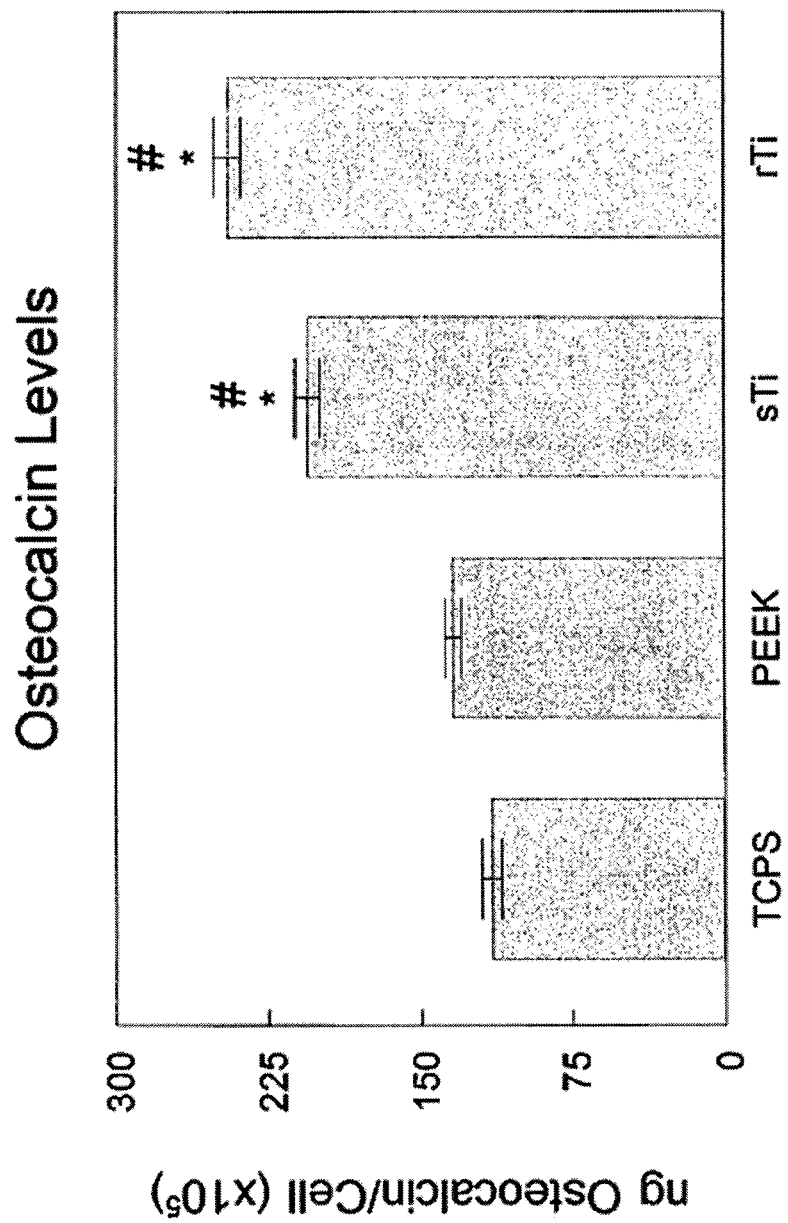
FIG. 15 shows a graph of osteocalcin levels for human MG63 osteoblast-like cells cultured on tissue culture polystyrene (TCPS), PEEK, sTI, and rTi surfaces.
Figure 16:
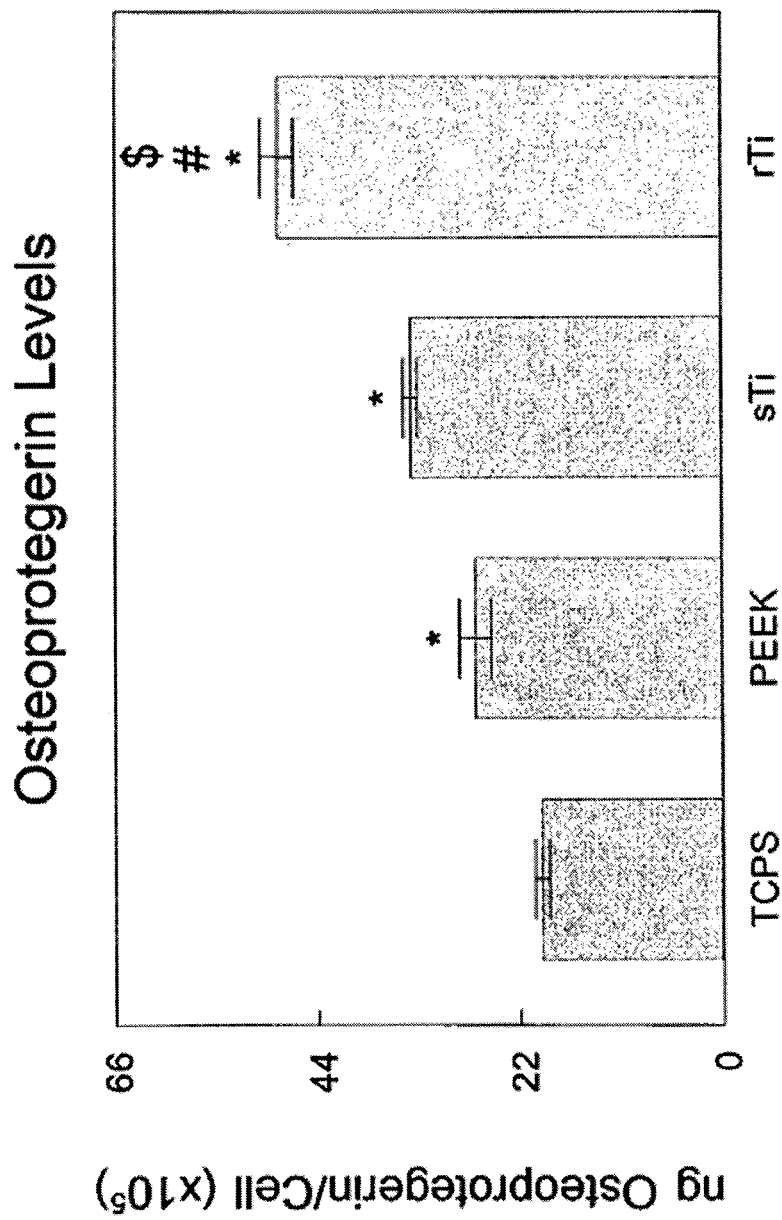
FIG. 16 shows a graph of osteoprotegerin levels for human MG63 osteoblast-like cells cultured on tissue culture polystyrene (TCPS), PEEK, sTI, and rTi surfaces.
Figure 17:
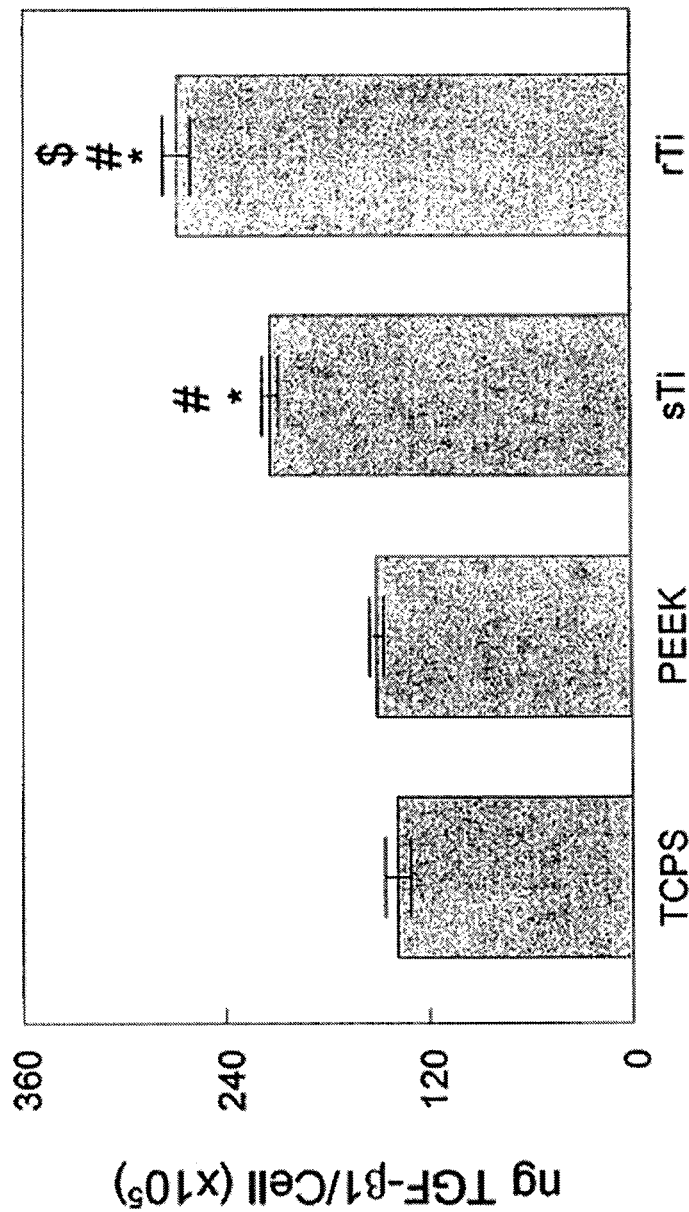
FIG. 17 shows a graph of latent TGF-β1 levels for human MG63 osteoblast-like cells cultured on tissue culture polystyrene (TCPS), PEEK, sTI, and rTi surfaces.
Figure 18:
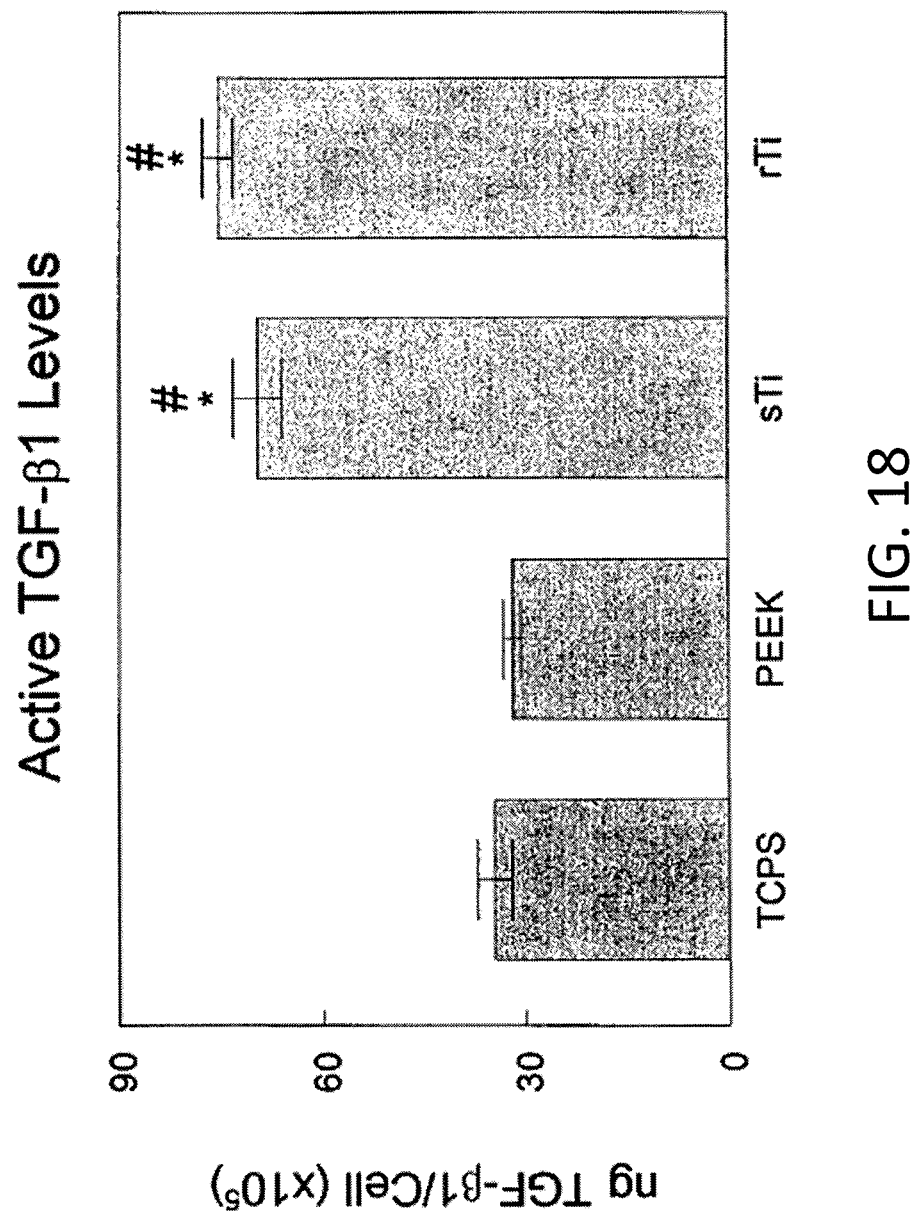
FIG. 18 shows a graph of active TGF-β1 levels for human MG63 osteoblast-like cells cultured on tissue culture polystyrene (TCPS), PEEK, sTI, and rTi surfaces.
Figure 19:
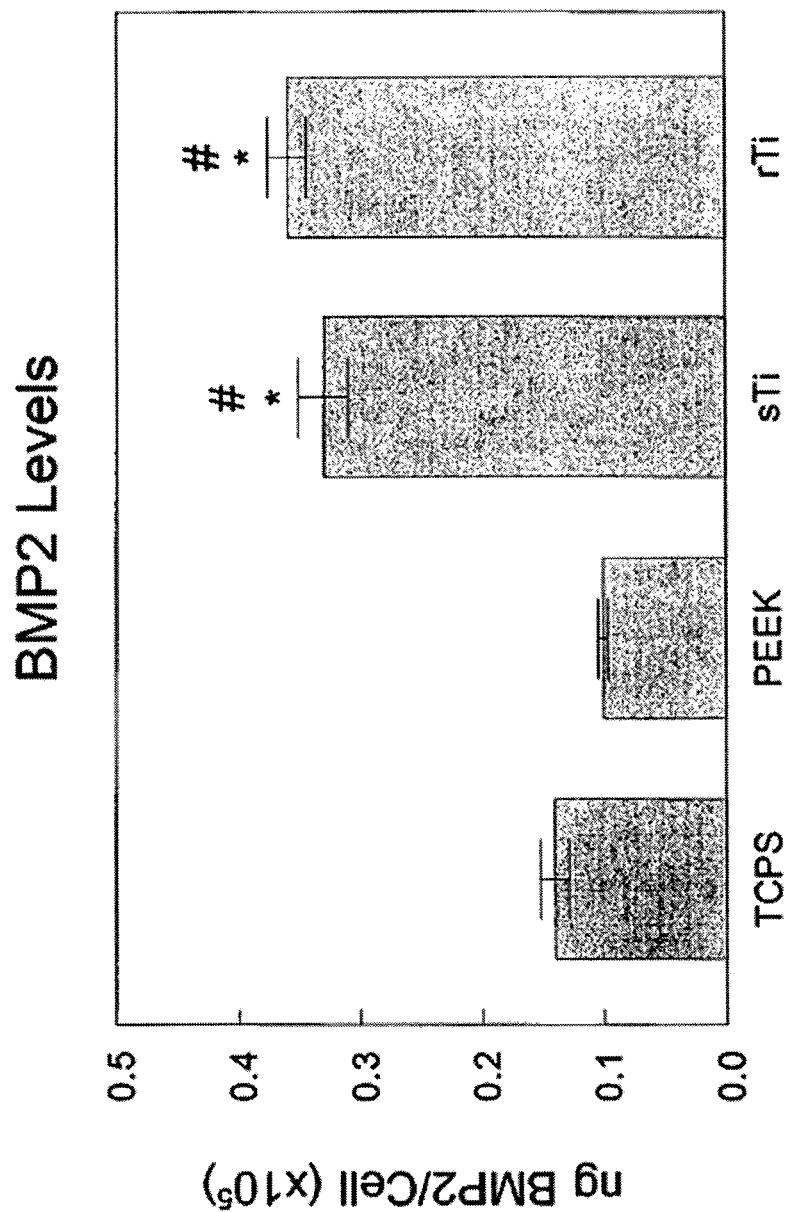
FIG. 19 shows a graph of BMP2 levels for human MG63 osteoblast-like cells cultured on tissue culture polystyrene (TCPS), PEEK, sTI, and rTi surfaces.
Figure 20:
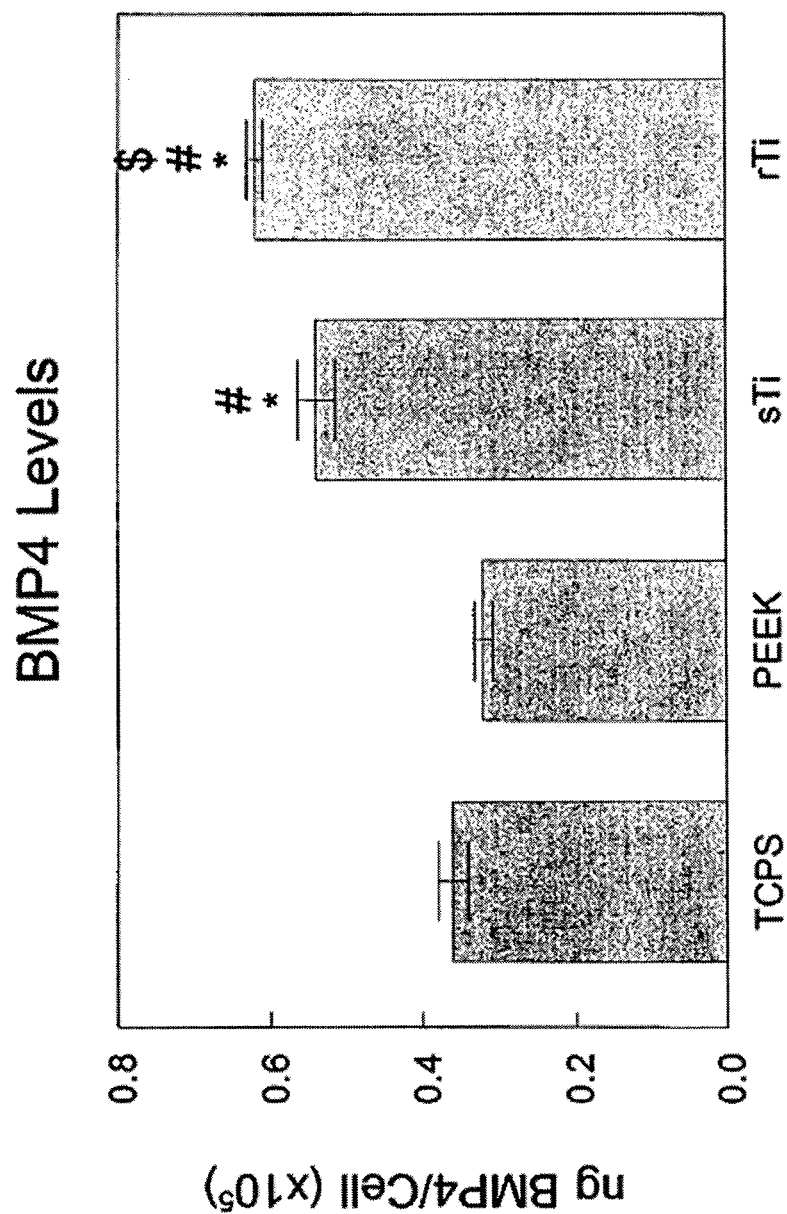
FIG. 20 shows a graph of active BMP4 levels for human MG63 osteoblast-like cells cultured on tissue culture polystyrene (TCPS), PEEK, sTI, and rTi surfaces.
Figure 21:
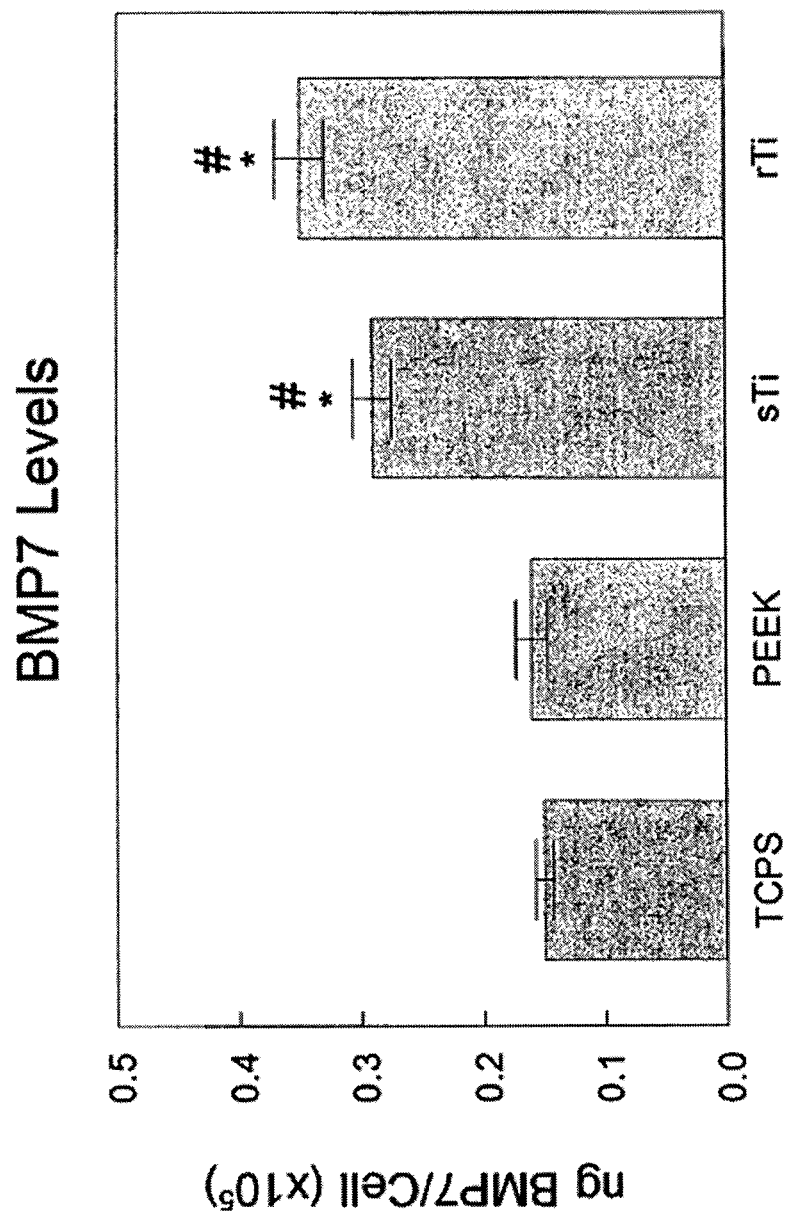
FIG. 21 shows a graph of active BMP7 levels for human MG63 osteoblast-like cells cultured on tissue culture polystyrene (TCPS), PEEK, sTI, and rTi surfaces.
Figure 22:
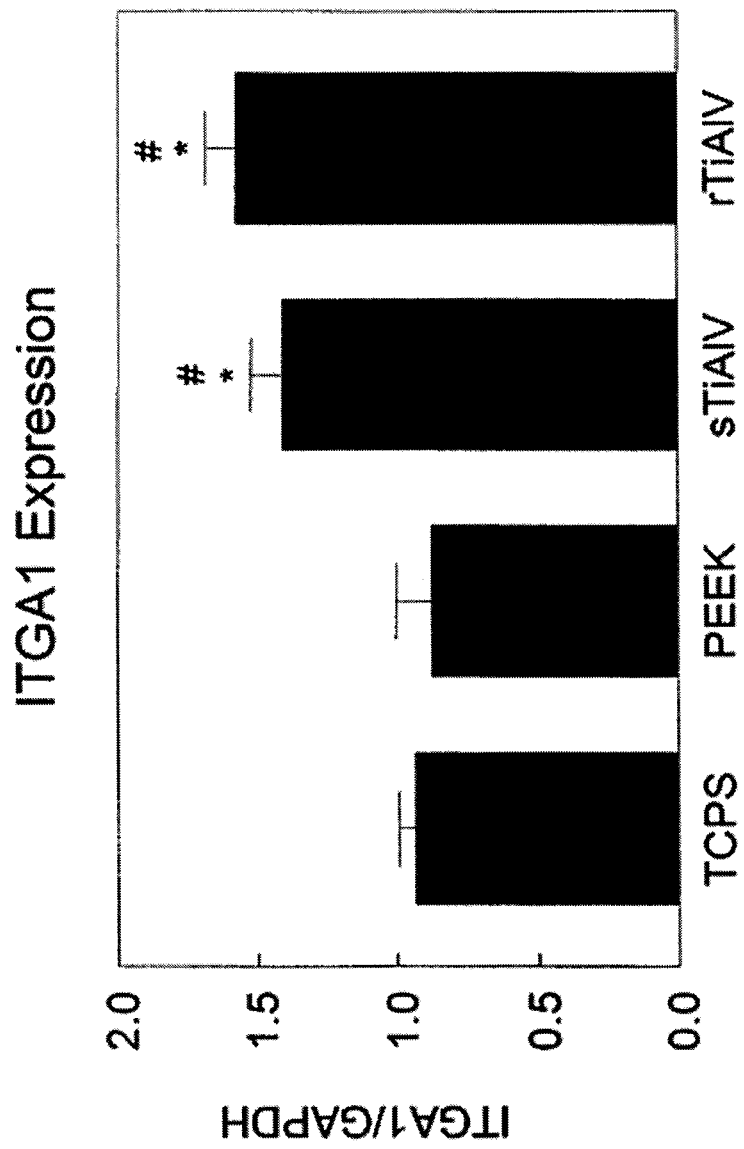
FIG. 22 shows a graph of ITGA1 expression for human MG63 osteoblast-like cells cultured on tissue culture polystyrene (TCPS), PEEK, sTI, and rTi surfaces.
Figure 23:
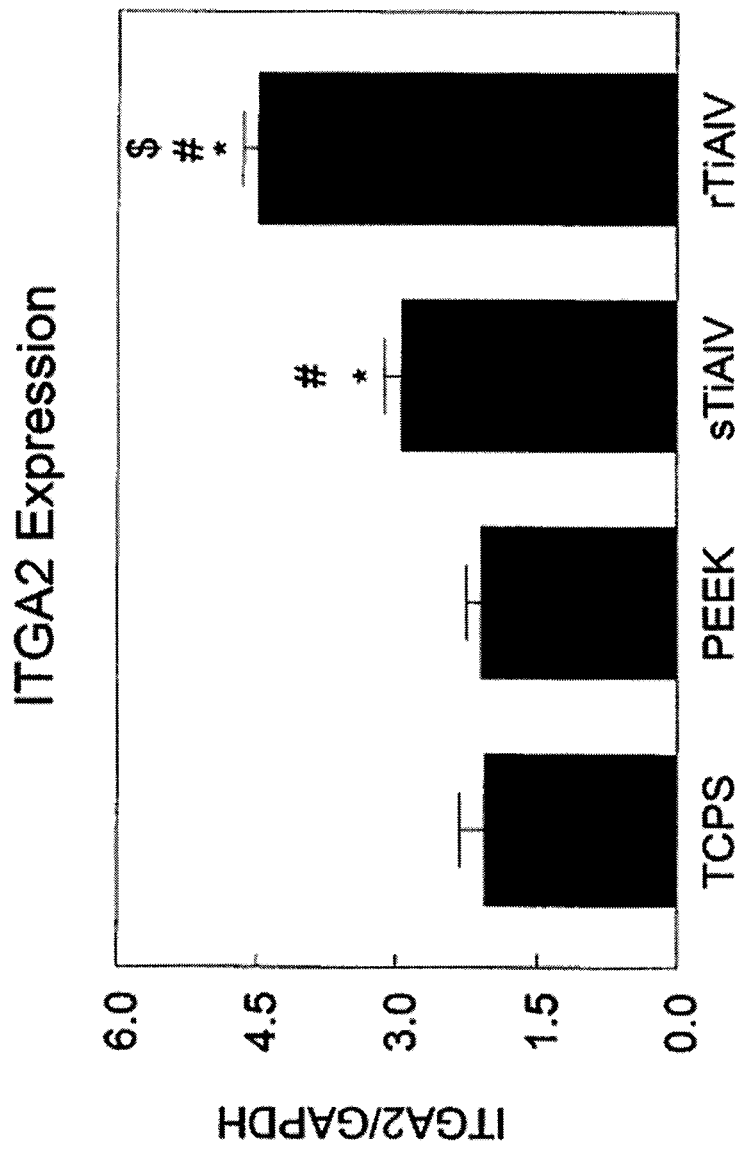
FIG. 23 shows a graph of ITGA2 expression for human MG63 osteoblast-like cells cultured on tissue culture polystyrene (TCPS), PEEK, sTI, and rTi surfaces.
Figure 24:
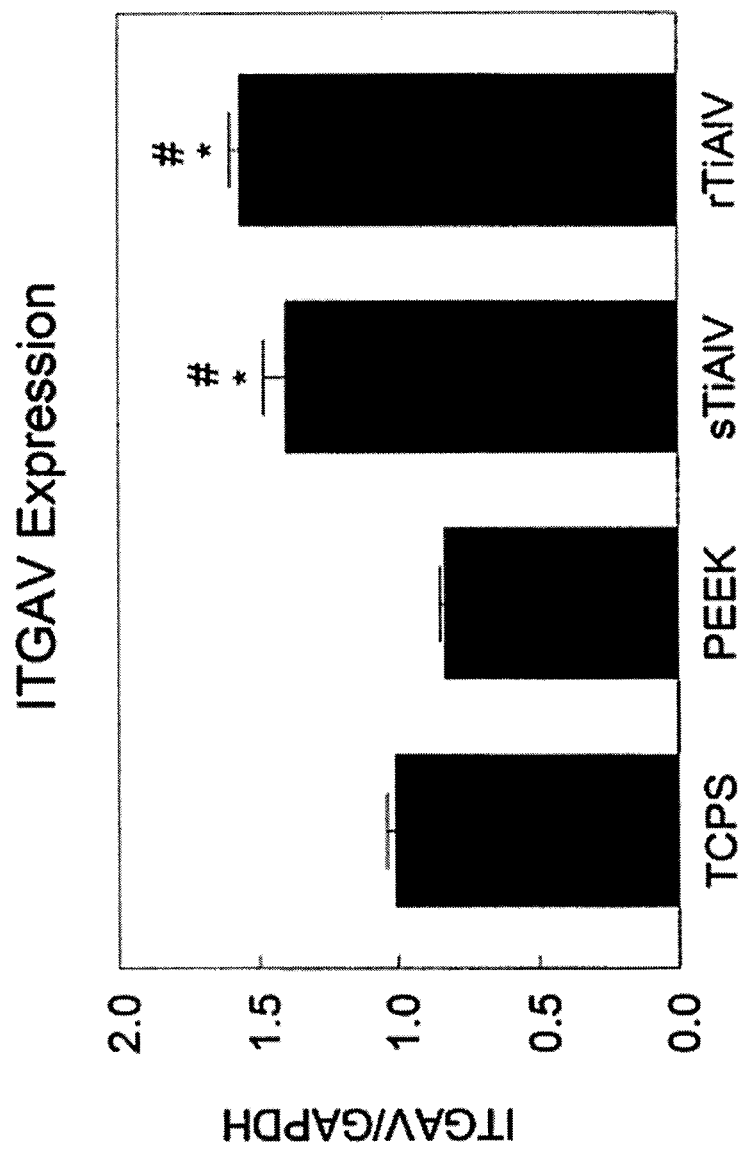
FIG. 24 shows a graph of ITGAV expression for human MG63 osteoblast-like cells cultured on tissue culture polystyrene (TCPS), PEEK, sTI, and rTi surfaces.
Figure 25:
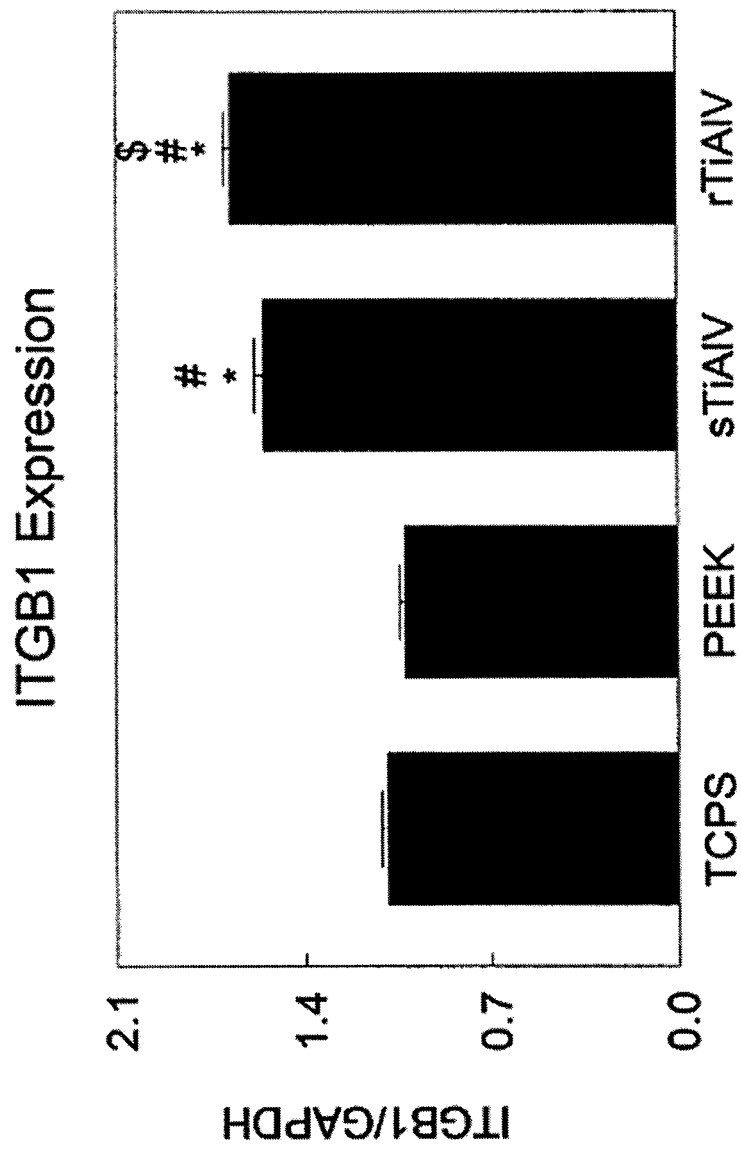
FIG. 25 shows a graph of ITGB1 expression for human MG63 osteoblast-like cells cultured on tissue culture polystyrene (TCPS), PEEK, sTI, and rTi surfaces.
Figure 26:
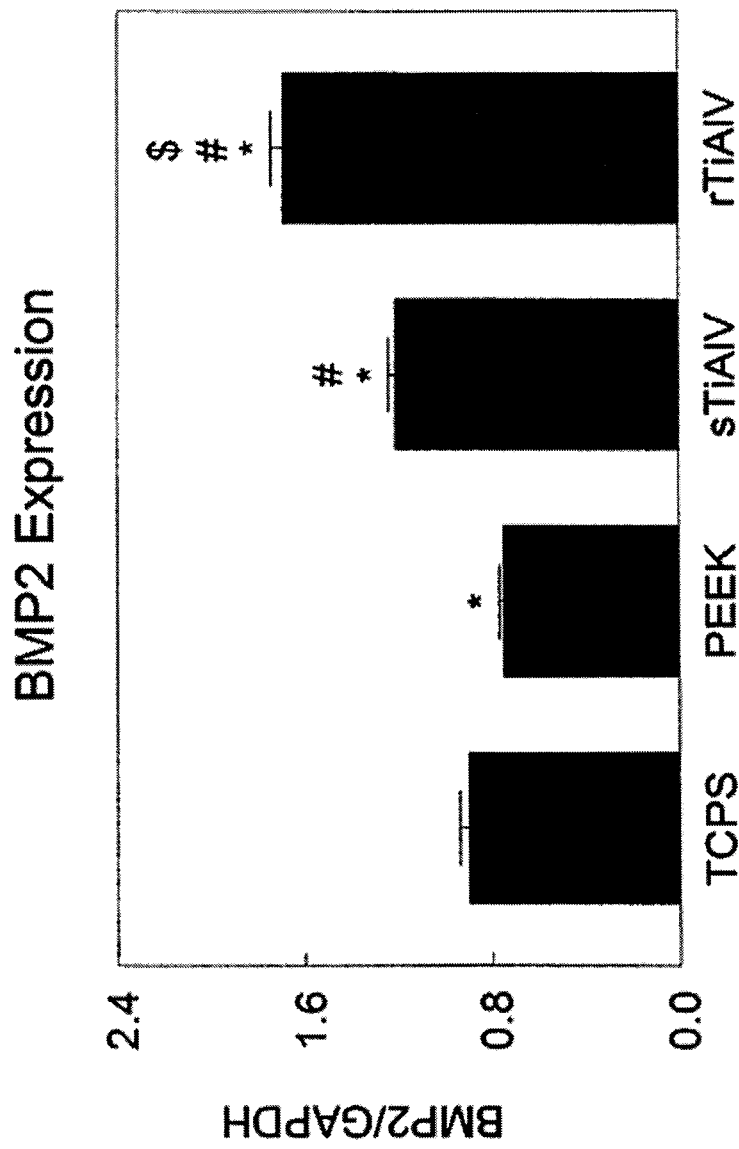
FIG. 26 shows a graph of BMP2 expression for human MG63 osteoblast-like cells cultured on tissue culture polystyrene (TCPS), PEEK, sTI, and rTi surfaces.
Figure 27:
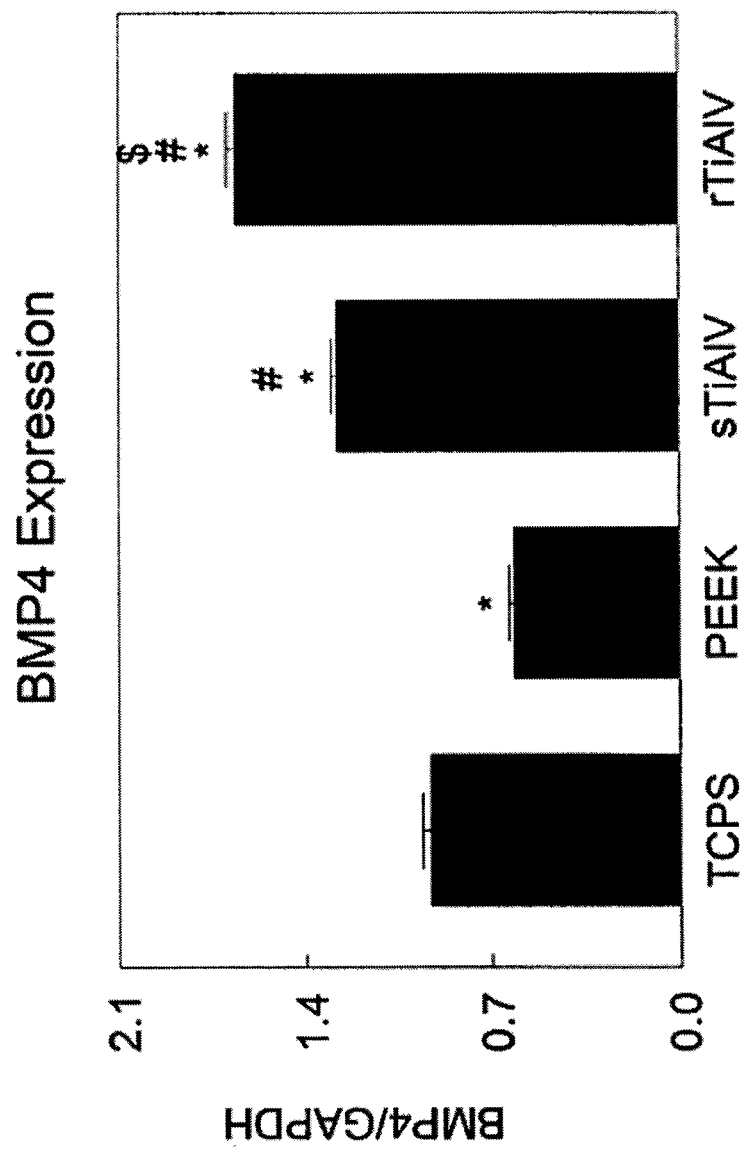
FIG. 27 shows a graph of BMP4 expression for human MG63 osteoblast-like cells cultured on tissue culture polystyrene (TCPS), PEEK, sTI, and rTi surfaces.
Figure 28:
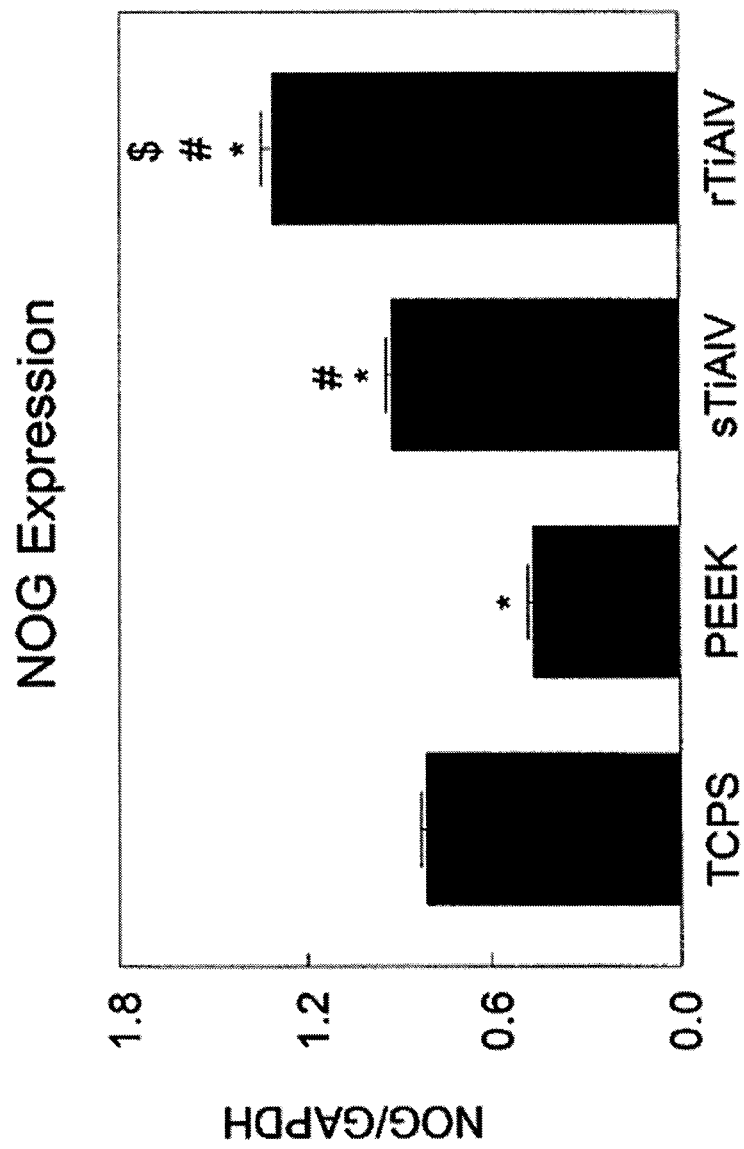
FIG. 28 shows a graph of NOG expression for human MG63 osteoblast-like cells cultured on tissue culture polystyrene (TCPS), PEEK, sTI, and rTi surfaces.
Figure 29:
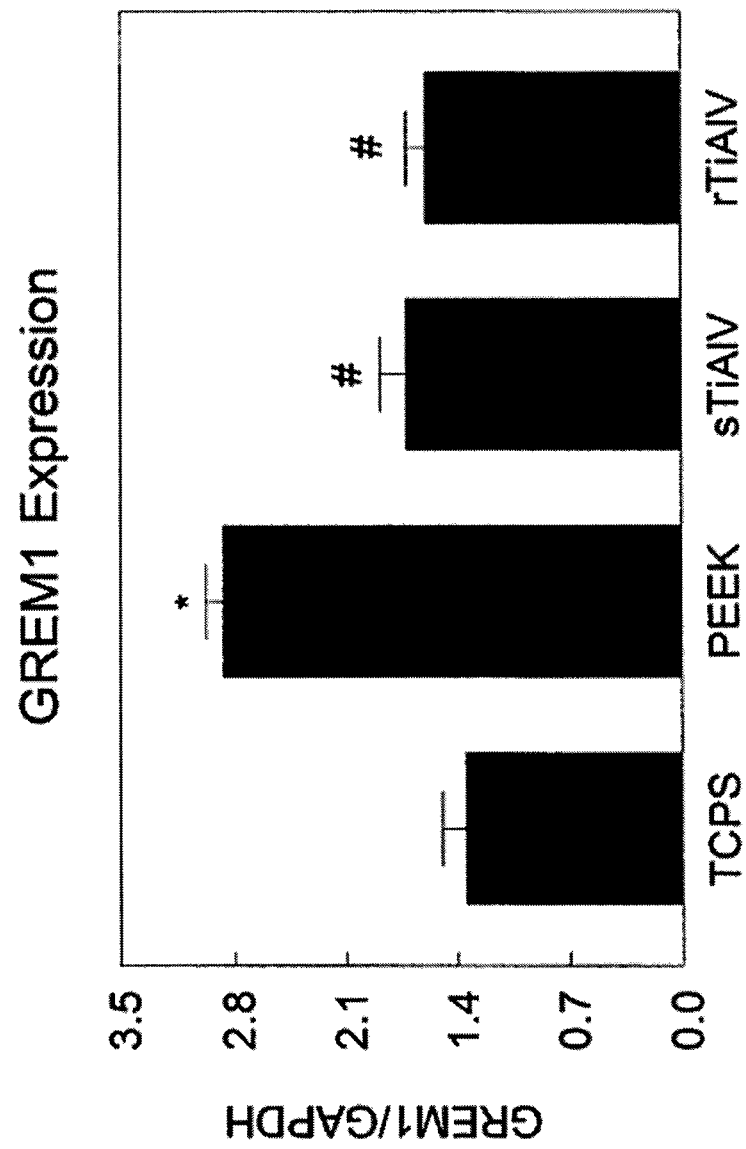
FIG. 29 shows a graph of GREM1 expression for human MG63 osteoblast-like cells cultured on tissue culture polystyrene (TCPS), PEEK, sTI, and rTi surfaces.

Test Method. Human osteoblast-like MG63 cells were cultured on tissue culture polystyrene (TCPS), PEEK, or smooth [sTi6Al4V] and rough [rTi6Al4V] surfaces. FIG. 7 shows a confocal laser microscopy image of the PEEK surface; FIG. 8 shows a confocal laser microscopy image of the sTiAlV surface; and FIG. 9 shows a confocal laser microscopy image of the rTiAlV surface. FIG. 10 shows a SEM image of the PEEK surface at 1000× and 20,000× magnification; FIG. 11 shows a SEM image of the sTiAlV surface at 1000× and 20,000× magnification; FIG. 12 shows a SEM image of the rTiAlV surface at 1000× magnification. Gene expression was measured by qPCR. Osteoblast maturation was assessed by analysis of cell number, alkaline phosphatase activity (ALP), and secreted osteocalcin, osteoprotegerin, TGFβ1, BMP2, BMP4, and BMP7. Data are mean±SEM (n=6/condition), analyzed by ANOVA with Bonferroni's modification of Student's t-test.

Human MG63 osteoblast-like cells were harvested 24 hours after confluence on TCPS. Cell number, alkaline phosphatase specific activity in cell lysates and levels of osteocalcin, osteoprotegerin, active TGFβ1, latent TGFβ1, BMP2 and BMP4 in the conditioned media were measured. The results of these measurements are shown in FIGS. 13-21, respectively. P-values were as follows: *p<0.05, v. TCPS; #p<0.05, v. PEEK; $p<0.05, v. sTiAlV.

Human MG63 osteoblast-like cells were harvested 12 hours after confluence on TCPS. Levels of mRNA for integrins alpha 1 (ITGA1), alpha 2 (ITGA2), alpha v (ITGAV), and beta 1 (ITGB1), BMP2 (A) and BMP4, and BMP inhibitors noggin (NOG) and gremlin 1 (GREM1) were measured by real-time qPCR and normalized to GAPDH. The results of these measurements are shown in FIGS. 22-29, respectively. P-values were as follows: *p<0.05, v. TCPS; #p<0.05, v. PEEK; $p<0.05, v. sTiAlV.

Results. The results indicated that osteoblasts on Ti6Al4V surfaces present a more mature phenotype than osteoblasts grown on PEEK. Cells on Ti6Al4V, but not PEEK, produced an osteogenic environment. Osteoblasts cultured on Ti6Al4V produced and regulated BMP pathway molecules, increasing BMP2, BMP4, BMP7, and physiologic BMP inhibitors. One reason for the differential responses of osteoblasts to PEEK and TiALV may have been from differences in integrin expression and downstream signaling by these receptors. Taken together, surface properties, including the composition of the bulk material, are important in directing cell response to implant materials, ultimately affecting implant success. The results demonstrated that Ti6Al4V surfaces positively modulate osteoblast maturation and regulated BMP signaling.

The invention is not limited to the embodiments described and exemplified above, but is capable of variation and modification within the scope of the appended claims.

What is claimed:

1. An interbody spinal implant, comprising:
a titanium or titanium alloy body having a top surface, a bottom surface, sides, and at least one aperture extending from the top surface to the bottom surface; and
internal surfaces having a roughened, irregular surface topography lacking symmetry, facilitating osseointegration and cellular attachment and osteoblast maturation, and including (a) macro-scale structural features having a maximum peak-to-valley height of about 40 microns to about 500 microns, (b) micro-scale structural features having a maximum peak-to-valley height of about 2 microns to about 40 microns, and (c) nano-scale structural features having a maximum peak-to-valley height of about 0.05 microns to about 5 microns, the three types of structural features overlapping.

2. The interbody spinal implant of claim 1, wherein the body further has at least one transverse aperture through each of the sides, and the transverse aperture comprises sidewalls comprising a roughened, irregular surface topography comprising micro-scale structural features having a maximum peak-to-valley height of about 2 microns to about 40 microns and nano-scale structural features having a maximum peak-to-valley height of about 0.05 microns to about 5 microns.

3. The interbody spinal implant of claim 1, wherein the body further has a rear wall comprising an internal surface comprising a roughened, irregular surface topography comprising micro-scale structural features having a maximum peak-to-valley height of about 2 microns to about 40 microns and nano-scale structural features having a maximum peak-to-valley height of about 0.05 microns to about 5 microns.

4. The interbody spinal implant of claim 1, wherein the macro-scale structural features further have an amplitude of about 20 microns to about 200 microns from a peak to a mean line, and a spacing of about 400 microns to about 2000 microns between the macro-scale structural features.

5. The interbody spinal implant of claim 1, wherein the micro-scale structural features further comprise an amplitude of about 1 micron to about 20 microns from a peak to a mean line and a spacing of about 20 microns to about 400 microns between the micro-scale structural features.

6. The interbody spinal implant of claim 1, wherein the nano-scale structural features further comprise an amplitude of about 0.01 microns to about 1 micron from a peak to a mean line and a spacing of about 0.1 microns to about 30 microns between the nano-scale structural features.

7. The interbody spinal implant of claim 6, wherein the spacing is about 0.5 microns to about 20 microns between nano-scale structural features.

8. The interbody spinal implant of claim 1, further comprising bone graft material disposed in the at least one aperture.

9. The interbody spinal implant of claim 1, wherein the body is generally oval-shaped in transverse cross section.

10. The interbody spinal implant of claim 1, wherein the body is generally rectangular-shaped in transverse cross section.

11. The interbody spinal implant of claim 1, wherein the body is generally curved-shaped in transverse cross section.

12. The interbody spinal implant of claim 1, wherein the at least one aperture is a single vertical aperture extending from the top surface to the bottom surface.

13. The interbody spinal implant of claim 12, wherein the single vertical aperture of the body has maximum width at its center and defines a transverse rim on the top surface and on the bottom surface, the transverse rim having a posterior thickness greater than an anterior thickness and having a blunt and radiused portion along the top of the sides.

14. The interbody spinal implant of claim 13, wherein the portion of the transverse rim that is not blunt and radiused has a roughened surface topography and wherein the blunt and radiused portion does not have any roughened surface topography.

15. An interbody spinal implant, comprising:
a titanium or titanium alloy body having a top surface, a bottom surface, sides, and at least one aperture extending from the top surface to the bottom surface; and
internal surfaces having a roughened, irregular surface topography lacking symmetry, facilitating osseointegration and cellular attachment and osteoblast maturation, and including (a) macro-scale structural features having a maximum peak-to-valley height of about 40 microns to about 500 microns, an amplitude of about 20 microns to about 200 microns from a peak to a mean line, and a spacing of about 20 microns to about 400 microns, (b) micro-scale structural features having a maximum peak-to-valley height of about 2 microns to about 40 microns, an amplitude of about 1 micron to about 20 microns from a peak to a mean line, and a spacing of about 20 microns to about 400 microns, and (c) nano-scale structural features having a maximum peak-to-valley height of about 0.05 microns to about 5 microns, an amplitude of about 0.01 microns to about 1 micron from a peak to a mean line, and a spacing of about 0.1 microns to about 30 microns, the three types of structural features overlapping.

16. The interbody spinal implant of claim 15, wherein the body further has at least one transverse aperture through each of the sides, and the transverse aperture comprises sidewalls comprising a roughened, irregular surface topography comprising micro-scale structural features having a maximum peak-to-valley height of about 2 microns to about 40 microns and nano-scale structural features having a maximum peak-to-valley height of about 0.05 microns to about 5 microns.

17. The interbody spinal implant of claim 15, wherein the body further has a rear wall comprising an internal surface comprising a roughened, irregular surface topography comprising micro-scale structural features having a maximum peak-to-valley height of about 2 microns to about 40 microns and nano-scale structural features having a maximum peak-to-valley height of about 0.05 microns to about 5 microns.

18. The interbody spinal implant of claim 15, further comprising bone graft material disposed in the at least one aperture.

19. The interbody spinal implant of claim 15, wherein the spacing is about 0.5 microns to about 20 microns between the nano-scale structural features.

20. The interbody spinal implant of claim 15, wherein the at least one aperture is a single vertical aperture extending from the top surface to the bottom surface, having a maximum width at its center, and defining a transverse rim on the top surface and on the bottom surface, the transverse rim having a posterior thickness greater than an anterior thickness and having a blunt and radiused portion along the top of the sides, wherein the portion of the transverse rim that is not blunt and radiused has a roughened surface topography and wherein the blunt and radiused portion does not have any roughened surface topography.

* * * * *